US008431398B2

(12) United States Patent
Knoblich et al.

(10) Patent No.: US 8,431,398 B2
(45) Date of Patent: Apr. 30, 2013

(54) METHODS FOR MODULATING THE PROLIFERATION AND DIFFERENTIATION POTENTIAL OF STEM CELLS AND PROGENITOR CELLS

(75) Inventors: Juergen Knoblich, Vienna (AT); Jens Schwamborn, Münster (DE)

(73) Assignee: IMBA-Institut fur Molekulare Biotechnologie GmbH, Vienna (AT)

( * ) Notice: Subject to any disclaimer, the term of this patent is extended or adjusted under 35 U.S.C. 154(b) by 199 days.

(21) Appl. No.: 12/680,493

(22) PCT Filed: Sep. 19, 2008

(86) PCT No.: PCT/EP2008/062568
§ 371 (c)(1),
(2), (4) Date: Aug. 27, 2010

(87) PCT Pub. No.: WO2009/040319
PCT Pub. Date: Apr. 2, 2009

(65) Prior Publication Data
US 2010/0317563 A1 Dec. 16, 2010

(30) Foreign Application Priority Data

Sep. 28, 2007 (EP) ..................... 07117501

(51) Int. Cl.
*C12N 5/02* (2006.01)
*C12N 15/11* (2006.01)
*C12N 15/13* (2006.01)

(52) U.S. Cl.
USPC .......... 435/377; 435/404; 435/183; 514/44 R; 514/44 A

(58) Field of Classification Search .................. None
See application file for complete search history.

(56) References Cited

U.S. PATENT DOCUMENTS

| 7,235,654 | B2 | 6/2007 | Li et al. ............... 536/24.5 |
| 2003/0143732 | A1 | 7/2003 | Fosnaugh et al. ......... 435/325 |
| 2007/0015145 | A1* | 1/2007 | Woolf et al. ............... 435/6 |
| 2007/0204352 | A1* | 8/2007 | Caldwell et al. .......... 800/12 |
| 2007/0218548 | A1 | 9/2007 | Nishikawa et al. ........ 435/325 |

FOREIGN PATENT DOCUMENTS

WO   WO 2005/113789    12/2005

OTHER PUBLICATIONS

Qian et al., Neuron. Oct. 2000;28(1):69-80.*
Schwamborn et al. Cell vol. 136, Issue 5, Mar. 6, 2009, pp. 913-925.*
Agrawal and Zhao, "Antisense therapeutics," *Curr. Opin. Chem. Biol.*, 2:519-528, 1998.
Albor et al., "The interaction of Piasy with Trim32, an E3-ubiquitin ligase mutated in limb-girdle muscular dystrophy type 2H, promotes Piasy degradation and regulates UVB-induced keratinocyte apoptosis through NFkappaB,"*J. Biol. Chem.*, 281:25850-66, 2006.
Auer, "HTS: understanding the physiology of life," *Drug Discovery Today*, 6:935-6, 2001.
Battey et al., "The human c-myc oncogene: structural consequences of translocation into the IgH locus in Burkitt lymphoma," GenBank Accession No. P01106, 2010.
Bennett et al., "Cationic lipids enhance cellular uptake and activity of phosphorothioate antisense oligonucleotides," *Mol. Pharmacol.*, 41:1023-33, 1992.
Berg et al., "Small-molecule antagonists of Myc/Max dimerization inhibit Myc-induced transformation of chicken embryo fibroblasts," *Proc. Natl. Acad. Sci. USA*, 99:3830-5, 2002.
Betschinger et al., "Asymmetric segregation of the tumor suppressor brat regulates self-renewal in *Drosophila* neural stem cells," *Cell*, 124:1241-53, 2006.
Birikh et al., "The structure, function and application of the hammerhead ribozyme," *Eur. J. Biochem.*, 245:1-16, 1997.
Borg et al., "Intragenic deletion of TRIM3 in compound heterozygotes with sarcotubular myopathy/LGMD2H," GenBank Accession No. NM_012210, 2010.
Braasch and Corey, "Novel antisense and peptide nucleic acid strategies for controlling gene expression," *Biochemistry*, 41:4503-10, 2002.
Brodeur et al., "Amplification of N-myc in untreated human neuroblastomas correlates with advanced disease stage," *Science*, 224:1121-4, 1984.
Brummelkamp et al., "A system for stable expression of short interfering RNAs in mammalian cells," *Science*, 296:550-553, 2002.
Brummelkamp et al., "Stable suppression of tumorigenicity by virus-mediated RNA interference," *Cancer Cell*, 2:243-7, 2002.
Buchschacher and Wong-Staal, "Development of lentiviral vectors for gene therapy for human diseases," *Blood*, 95:2499-2504, 2000.
Calegari et al., "Tissue-specific RNA interference in postimplantation mouse embryos with endoribonuclease-prepared short interfering RNA," *Proc. Natl. Acad. Sci. USA*, 99:14236-40, 2002.
Calin et al., "Frequent deletions and down-regulation of micro-RNA genes miR15 and miR16 at 13q14 in chronic lymphocytic leukemia," *Proc. Natl. Acad. Sci. USA*, 99:15524-9, 2002.
Calin et al., "MicroRNA profiling reveals distinct signatures in B cell chronic lymphocytic leukemias," *Proc. Natl. Acad. Sci. USA*, 101:11755-60, 2004.
Chiang et al., "Homozygosity mapping with SNP arrays identifies TRIM32, an E3 ubiquitin ligase, as a Bardet-Biedl syndrome gene (BBS11)," *Proc. Natl. Acad. Sci. USA*, 103:6287-92, 2006.
Conti et al., "Niche-independent symmetrical self-renewal of a mammalian tissue stem cell," *PLoS Biol.*, 3:e283, 2005.
Cooper, "Optical biosensors: where next and how soon?" *Drug Discovery Today*, 11:1061-7, 2006.
Earnshaw and Gait, "Progress toward the structure and therapeutic use of the hairpin ribozyme," *Antisense Nucleic Acid Drug Dev.*, 7:403-11, 1997.

(Continued)

*Primary Examiner* — Daniel C Gamett
(74) *Attorney, Agent, or Firm* — Fulbright & Jaworski L.L.P.

(57) ABSTRACT

Modulators of TRIM-NHL proteins and their use for modulating the proliferation and differentiation potential of stem cells and progenitor cells. Inhibitors of TRIM-NHL proteins, e.g. TRIM32, are useful for stem cell maintenance in vitro and in vivo. Assay methods for identifying TRIM-NHL protein modulators make use of the E3 ligase activity of TRIM32 or its interaction with Argonaute-1.

20 Claims, 5 Drawing Sheets

OTHER PUBLICATIONS

Eigen and Rigler, "Sorting single molecules: application to diagnostics and evolutionary biotechnology," *Proc. Natl. Acad. Sci. USA*, 91:5740-7, 1994.

Elbashir et al., "Duplexes of 21-nucleotide RNAs mediate RNA interference in cultured mammalian cells," *Nature*, 411:494-498, 2001.

Felsher and Bishop, "Reversible tumorigenesis by MYC in hematopoietic lineages," *Mol. Cell.*, 4:199-207, 1999.

Follenzi and Naldini, "Generation of HIV-1 derived lentiviral vectors," *Methods Enzymol.*, 346:454-65, 2002.

Galderisi et al., "Antisense oligonucleotides as therapeutic agents," *J. Cell Physiol.*, 181:251-7, 1999.

Garraway and Sellers, "Lineage dependency and lineage-survival oncogenes in human cancer," *Nat. Rev. Cancer*, 6:593-602, 2006.

Gershkovich and Kholodovych, "Fluorogenic substrates for proteases based on intramolecular fluorescence energy transfer (IFETS)," *J. Biochem. Biophys. Meth.*, 33:135-62, 1996.

Gewirtz, "Antisense oligonucleotide therapeutics for human leukemia," *Curr. Opin. Hematol.*, 5:59-71, 1998.

Grandori and Eisenman, "Myc target genes," *Trends Biochem. Sci.*, 22:177-81, 1997.

Hampel, "The hairpin ribozyme: discovery, two-dimensional model, and development for gene therapy," *Prog. Nucleic Acid Res.*, 58:1-39, 1998.

Hatfield and Vierstra, "Multiple forms of ubiquitin-activating enzyme E1 from wheat. Identification of an essential cysteine by in vitro mutagenesis," *J. Biol. Chem.*, 267:14799-803, 1992.

Hatfield et al., Cloning of ubiquitin activating enzyme from wheat and expression of a functional protein in EsGenBank Accession No. M555604, 1993.

Hatfield et al., "Cloning of ubiquitin activating enzyme from wheat and expression of a functional protein in *Escherichia coli*," *J. Biol. Chem.*, 265:15813-7, 1990.

He et al., "A flow cytometric method to detect protein-protein interaction in living cells by directly visualizing donor fluorophore quenching during CFP—>YFP fluorescence resonance energy transfer (FRET)," *Cytometry*, 55:71-85, 2003.

He et al., "A microRNA polycistron as a potential human oncogene," *Nature*, 435:828-33, 2005.

Höglinger et al., "Dopamine depletion impairs precursor cell proliferation in Parkinson disease," *Nat. Neurosci.*, 7:726-35, 2004.

Hosseinkhani et al., "DNA nanoparticles encapsulated in 3D tissue-engineered scaffolds enhance osteogenic differentiation of mesenchymal stem cells," *J. Biomed. Mater. Res. A*, pp. 47-60, 2007.

Irie et al., "Therapeutic efficacy of an adenovirus-mediated anti-H-ras ribozyme in experimental bladder cancer," *Antisense Nucleic Acid Drug Dev.*, 9:341-9, 1999.

Jain et al., "Sustained loss of a neoplastic phenotype by brief inactivation of MYC," *Science*, 297:102-4, 2002.

Jensen et al., "Identification of a family of closely related human ubiquiten conjugating enzymes," GenBank Accession No. U39317, 1996.

Kafri et al., "A packaging cell line for lentivirus vectors," *J. Virol.*, 73:576-584, 1999.

Kanamoto et al., "Cloning and regulation of the vertebrate homologue of lin-41 that functions as a heterochronic gene in *Caenorhabditis elegans*," *Dev. Dyn.*, 235:1142-9, 2006.

Kettling et al., "Real-time enzyme kinetics monitored by dual-color fluorescence cross-correlation spectroscopy," *Proc. Natl. Acad. Sci. USA*, 95:1416-20, 1998.

Koesters et al., "Human eukaryotic initiation factor EIF2C1 gene: cDNA sequence, genomic organization, localization to chromosomal bands 1p34-p35, and expression," GenBank Accession No. Q9UL18, 2010.

Koltermann et al., "Rapid assay processing by integration of dual-color fluorescence cross-correlation spectroscopy: high throughput screening for enzyme activity," *Proc. Natl. Acad. Sci. USA*, 95:1421-6, 1998.

Kore and Eckstein, "Hammerhead ribozyme mechanism: a ribonucleotide 5' to the substrate cleavage site is not essential," *Biochemistry*, 38:10915-8, 1999.

Kudryashova et al., "Defciency of the E3 ubiquitin ligase TRIM32 mutations involves both neurogenic and myogenic characteristics," GenBank Accession No. NM_053084, 2010.

Kudryashova et al., "Trim32 is a ubiquitin ligase mutated in limb girdle muscular dystrophy type 2H that binds to skeletal muscle myosin and ubiquitinates actin," *J. Mol. Biol.*, 354:413-24, 2005.

Lancman et al., "Analysis of the regulation of lin-41 during chick and mouse limb development," *Dev. Dyn.*, 234:948-60, 2005.

Lappalainen et al., "Cationic liposomes mediated delivery of antisense oligonucleotides targeted to HPV 16 E7 mRNA in CaSki cells," *Antiviral Res.*, 23:119-130, 1994.

Lever, "HIV and other lentivirus-based vectors," *Gene Ther.*, 3:470-1, 1996.

Li et al., "The use of the R6 transgenic mouse models of Huntington's disease in attempts to develop novel therapeutic strategies," *NeuroRx*, 2:447-64, 2005.

Lin et al., "Human TRIM71 and its nematode homologue are targets of let-7 microRNA and its zebrafish orthologue is essential for development," *Mol. Biol. Evol.*, 24:2525-34, 2007.

Luther-Wyrsch et al., "Stable transduction with lentiviral vectors and amplification of immature hematopoietic progenitors from cord blood of preterm human fetuses," *Hum. Gene Ther.*, 12:377-89, 2001.

Magde et al., "Fluorescence correlation spectroscopy. II. An experimental realization," *Biopolymers*, 13:29-61, 1974.

Maiti et al., "Fluorescence correlation spectroscopy: diagnostics for sparse molecules," *Proc. Natl. Acad. Sci. USA*, 94:11753-7, 1997.

Matayoshi et al., "Novel fluorogenic substrates for assaying retroviral proteases by resonance energy transfer," *Science*, 247:954-8, 1990.

Morgan et al., "Development of a pentylenetetrazole-induced seizure model to evaluate kinase inhibitor efficacy in the central nervous system," *Neuroscience Lett.*, 395:143-8, 2006.

Murray, "Cell cycle extracts," *Methods Cell Biol.*, 36:581-605, 1991.

Okita et al., "Generation of germline-competent induced pluripotent stem cells," *Nature*, 448:313-7, 2007.

Pelengaris et al., "c-MYC: more than just a matter of life and death," *Nat. Rev. Cancer*, 2:764-7, 2002.

Rigler and Widengren, "Ultrasensitive detection of single molecules by fluorescence correlation spectroscopy," *Bioscience*, 3:180-3, 1990.

Rigler et al., "Fluorescence correlation spectroscopy with high count rate and low background—analysis of translation diffusion," *Eur. Biophys. J.*, 22:169-175, 1993.

Rogers, "Light on high-throughput screening: fluorescence-based assay technologies," *Drug Discovery Today*, 2:156-160, 1997.

Ross et al., "Systematic variation in gene expression patterns in human cancer cell lines," *Nat. Genet.*, 24:227-35, 2000.

Schwab et al., "Amplified DNA with limited homology to myc cellular oncogene is shared by human neuroblastoma cell lines and a neuroblastoma tumour," *Nature*, 305:245-8, 1983.

Schwille et al., "Dual-color fluorescence cross-correlation spectroscopy for multicomponent diffusional analysis in solution," *Biophys. J.*, 72:1878-86, 1997.

Selvin, "The renaissance of fluorescence resonance energy transfer," *Nature Structural Biol.*, 7:730-4, 2000.

Shu et al., "Doublecortin-like kinase controls neurogenesis by regulating mitotic spindles and M phase progression," *Neuron*, 49:25-39, 2006.

Smith et al., "Efficient expression by an alphavirus replicon of a functional ribozyme targeted to human immunodeficiency virus type 1," *J. Virol.*, 71:9713-21, 1997.

Spinola et al., "A new polymorphism (Ser362Thr) of the L-myc gene is not associated with lung adenorcarcinoma risk and prognosis," GenBank Accession No. AAO38672, 2004.

Stanton et al., "Nucleotide sequence of the human N-myc gene," GenBank Accession No. P04198, 2010.

Stark et al., "Not miR-ly muscular: microRNAs and muscle development," *Genes Dev.*, 19:2261-4, 2005.

Strausberg et al., "Generation and initial analysis of more than 15,000 full-length human and mouse cDNA sequences," GenBank Accession No. AAH05980, 2006.

Strausberg et al., "Generation and initial analysis of more than 15,000 full length human and mouse cDNA sequences," GenBank Accession No. AAH66917, 2006.

Sui et al., "A DNA vector-based RNAi technology to suppress gene expression in mammalian cells," *Proc. Natl. Acad. Sci. USA*, 99:5515-20, 2002.

Thews et al., "Cross talk free fluorescence cross correlation spectroscopy in live cells," *Biophys. J.*, 89:2069-76, 2005.

Vaish et al., "Recent developments in the hammerhead ribozyme field," *Nucleic Acids Res.*, 26:5237-42, 1998.

van de Wetering et al., "The beta-catenin/TCF-4 complex imposes a crypt progenitor phenotype on colorectal cancer cells," *Cell*, 111:241-50, 2002.

VandenDriessche et al., "Oncoretroviral and lentiviral vector-mediated gene therapy," *Methods Enzymol.*, 346:573-89, 2002.

Werning et al., "In vitro reprogramming of fibroblasts into a pluripotent ES-cell-like state," *Nature*, 448:318-24, 2007.

Winner et al., "Striatal deafferentation increases dopaminergic neurogenesis in the adult olfactory bulb," *Experimental Neurology*, 197:113-121, 2006.

Yokota et al., "Brain site-specific gene expression analysis in Alzheimer's disease patients," *Eur. J. Clin. Invest.*, 36:820-30, 2006.

Yu et al., "RNA interference by expression of short-interfering RNAs and hairpin RNAs in mammalian cells," *Proc. Natl. Acad. Sci. USA*, 99:6047-52, 2002.

\* cited by examiner

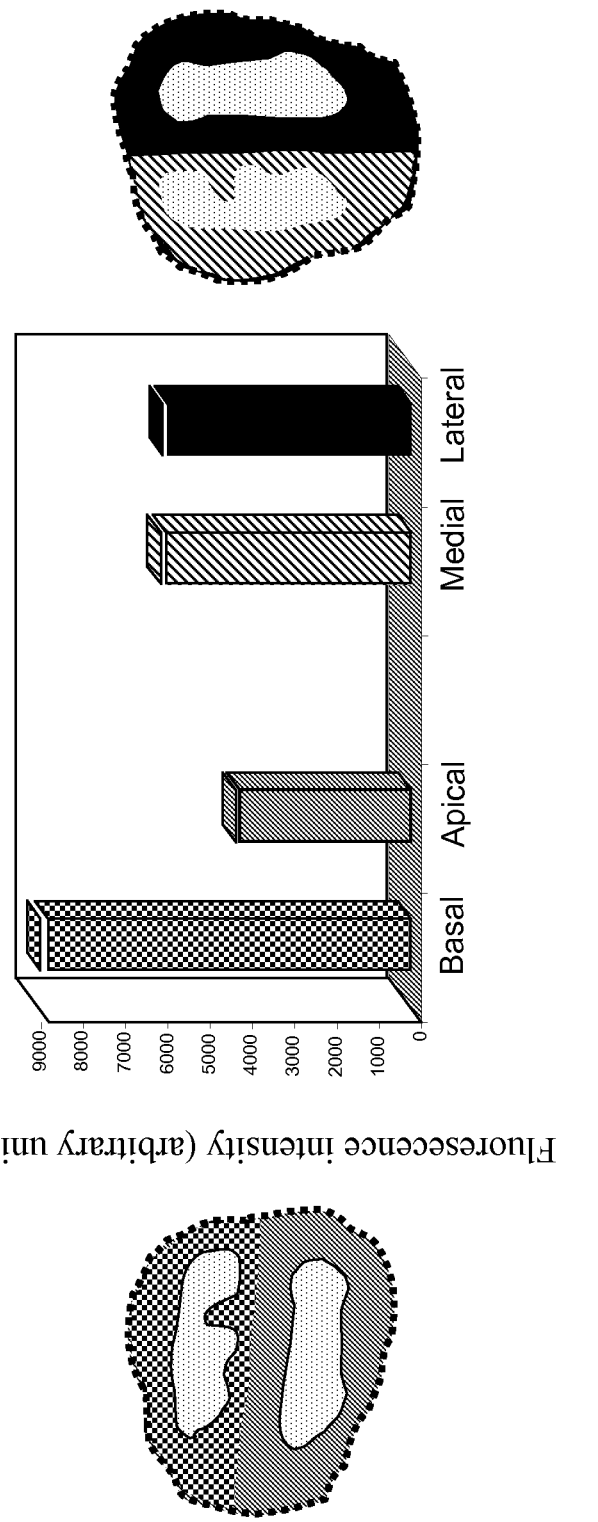

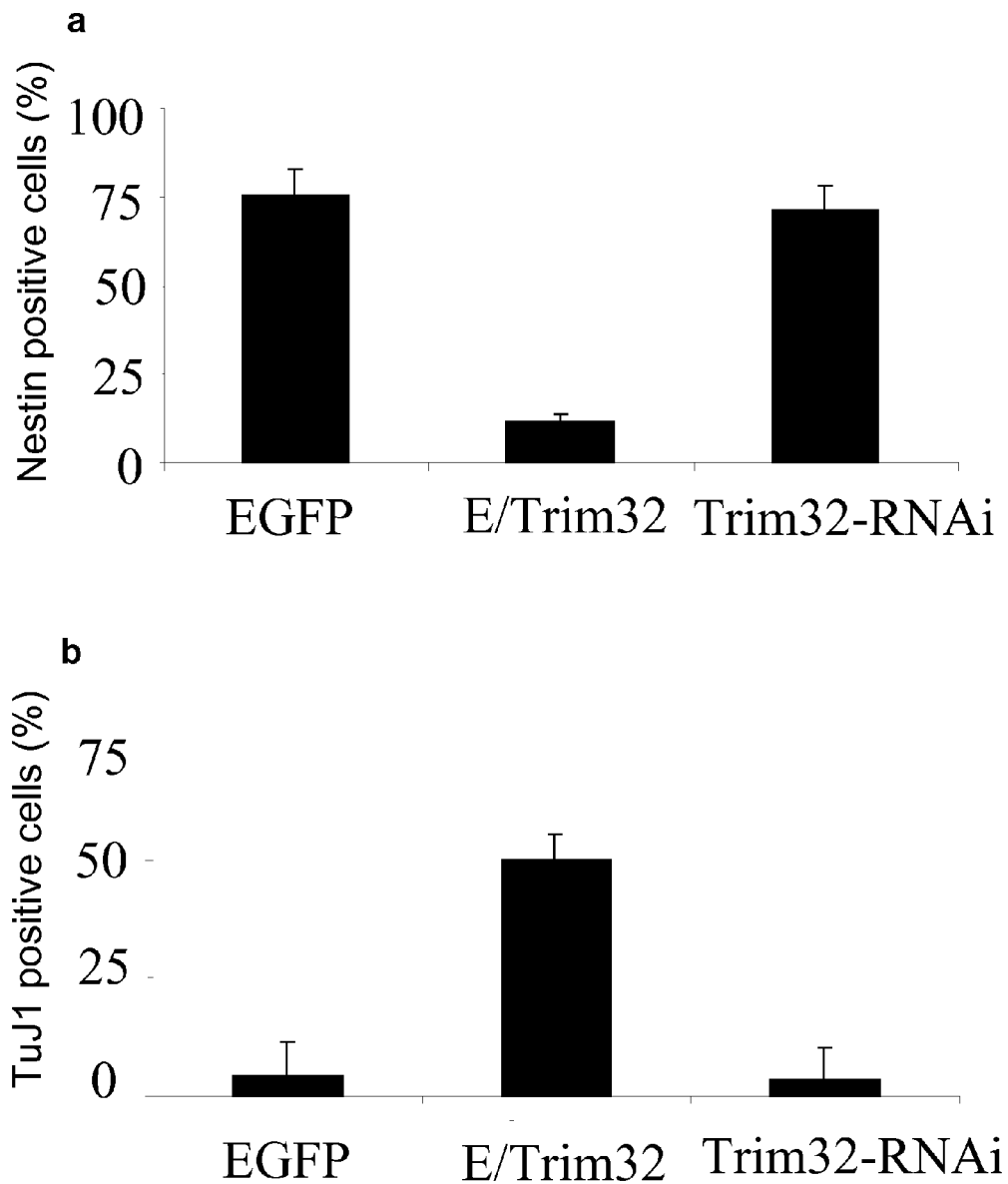
Fig. 2 a,b

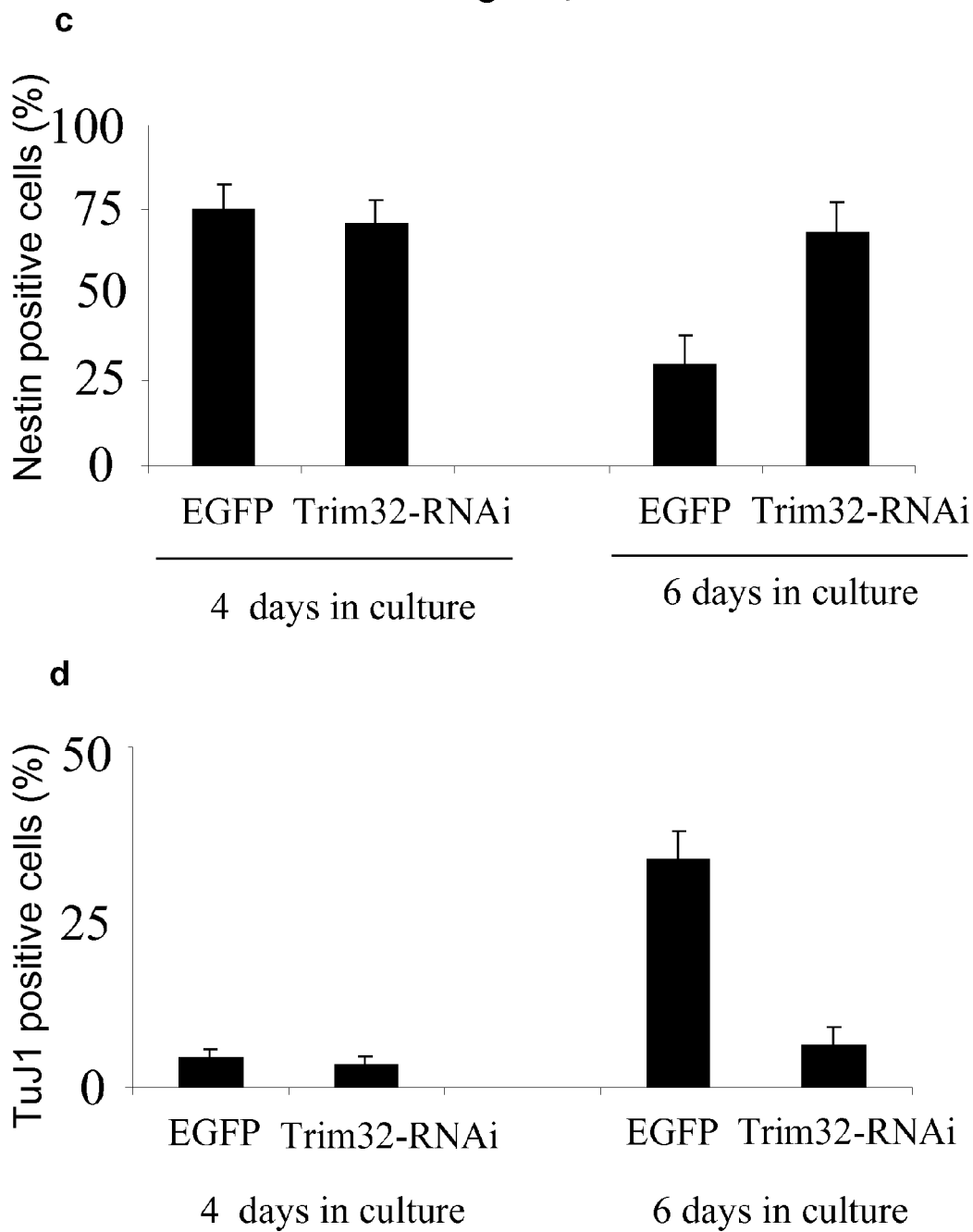

Fig. 4
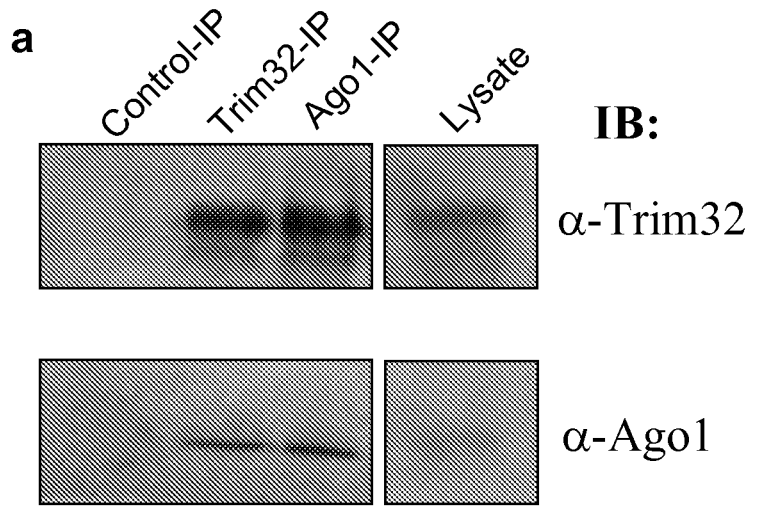
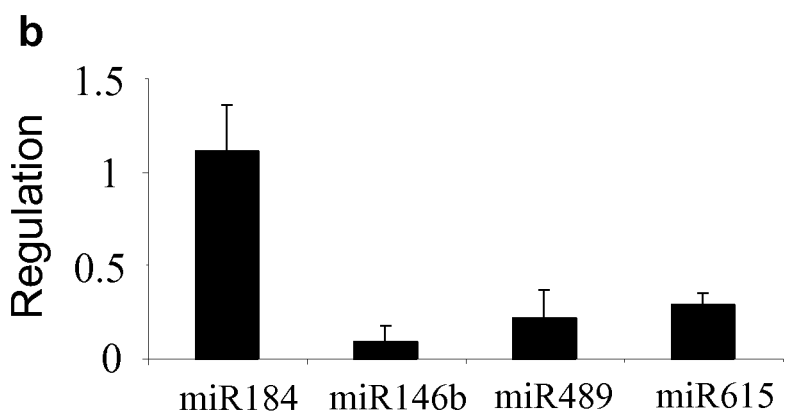
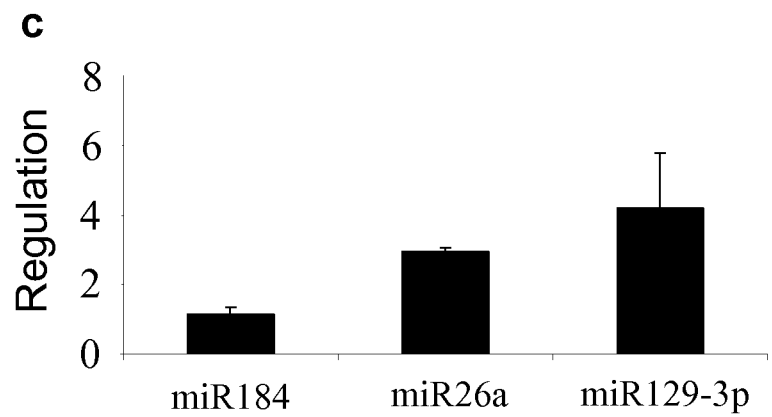

SEQUENCE LISTING

```
<160> NUMBER OF SEQ ID NOS: 7

<210> SEQ ID NO 1
<211> LENGTH: 1962
<212> TYPE: DNA
<213> ORGANISM: Homo sapiens
<220> FEATURE:
<221> NAME/KEY: CDS
<222> LOCATION: (1)..(1962)

<400> SEQUENCE: 1 atg gct gca gca gca gct tct cac ctg aac ctg gat gcc ctc cgg gaa        48
Met Ala Ala Ala Ala Ala Ser His Leu Asn Leu Asp Ala Leu Arg Glu
1               5                   10                  15 gtg cta gaa tgc ccc atc tgc atg gag tcc ttc aca gaa gag cag ctg        96
Val Leu Glu Cys Pro Ile Cys Met Glu Ser Phe Thr Glu Glu Gln Leu
            20                  25                  30 cgt ccc aag ctt ctg cac tgt ggc cat acc atc tgc cgc cag tgc ctg       144
Arg Pro Lys Leu Leu His Cys Gly His Thr Ile Cys Arg Gln Cys Leu
        35                  40                  45 gag aag cta ttg gcc agt agc atc aat ggt gtc cgc tgt ccc ttt tgc       192
Glu Lys Leu Leu Ala Ser Ser Ile Asn Gly Val Arg Cys Pro Phe Cys
    50                  55                  60 agc aag att acc cgc ata acc agc ttg acc cag ctg aca gac aat ctg       240
Ser Lys Ile Thr Arg Ile Thr Ser Leu Thr Gln Leu Thr Asp Asn Leu
65                  70                  75                  80 aca gtg cta aag atc att gat aca gct ggg ctc agc gag gct gtg ggg       288
Thr Val Leu Lys Ile Ile Asp Thr Ala Gly Leu Ser Glu Ala Val Gly
                85                  90                  95 ctg ctc atg tgt cgg tcc tgt ggg cgg cgt ctg ccc cgg caa ttc tgc       336
Leu Leu Met Cys Arg Ser Cys Gly Arg Arg Leu Pro Arg Gln Phe Cys
            100                 105                 110 cgg agc tgt ggt ttg gtg tta tgt gag ccc tgc cgg gag gca gac cat       384
Arg Ser Cys Gly Leu Val Leu Cys Glu Pro Cys Arg Glu Ala Asp His
        115                 120                 125 cag cct cct ggc cac tgt aca ctc cct gtc aaa gaa gca gct gag gag       432
Gln Pro Pro Gly His Cys Thr Leu Pro Val Lys Glu Ala Ala Glu Glu
    130                 135                 140 cgg cgt cgg gac ttt gga gag aag tta act cgt ctg cgg gaa ctt atg       480
Arg Arg Arg Asp Phe Gly Glu Lys Leu Thr Arg Leu Arg Glu Leu Met
145                 150                 155                 160 ggg gag ctg cag cgg cgg aag gca gcc ttg gaa ggt gtc tcc aag gac       528
Gly Glu Leu Gln Arg Arg Lys Ala Ala Leu Glu Gly Val Ser Lys Asp
                165                 170                 175 ctt cag gca agg tat aaa gca gtt ctc cag gag tat ggg cat gag gag       576
Leu Gln Ala Arg Tyr Lys Ala Val Leu Gln Glu Tyr Gly His Glu Glu
            180                 185                 190
```

|  |  |
|---|---:|
| cgc agg gtc cag gat gag ctg gct cgc tct cgg aag ttc ttc aca ggc<br>Arg Arg Val Gln Asp Glu Leu Ala Arg Ser Arg Lys Phe Phe Thr Gly<br>           195                    200                    205 | 624 |
| tct ttg gct gaa gtt gag aag tcc aat agt caa gtg gta gag gag cag<br>Ser Leu Ala Glu Val Glu Lys Ser Asn Ser Gln Val Val Glu Glu Gln<br>210                    215                    220 | 672 |
| agt tac ctg ctt aac att gca gag gtg cag gct gtg tct cgc tgt gac<br>Ser Tyr Leu Leu Asn Ile Ala Glu Val Gln Ala Val Ser Arg Cys Asp<br>225                    230                    235                    240 | 720 |
| tac ttc ctg gcc aag atc aag cag gca gat gta gca cta ctg gag gag<br>Tyr Phe Leu Ala Lys Ile Lys Gln Ala Asp Val Ala Leu Leu Glu Glu<br>                    245                    250                    255 | 768 |
| aca gct gat gag gag gag cca gag ctc act gcc agc ttg cct cgg gag<br>Thr Ala Asp Glu Glu Glu Pro Glu Leu Thr Ala Ser Leu Pro Arg Glu<br>            260                    265                    270 | 816 |
| ctc acc ctg caa gat gtg gag ctc ctt aag gta ggt cat gtt ggc ccc<br>Leu Thr Leu Gln Asp Val Glu Leu Leu Lys Val Gly His Val Gly Pro<br>        275                    280                    285 | 864 |
| ctc caa att gga caa gct gtt aag aag ccc cgg aca gtt aac gtg gaa<br>Leu Gln Ile Gly Gln Ala Val Lys Lys Pro Arg Thr Val Asn Val Glu<br>        290                    295                    300 | 912 |
| gat tcc tgg gcc atg gag gcc aca gcg tct gct gcc tct acc tct gtt<br>Asp Ser Trp Ala Met Glu Ala Thr Ala Ser Ala Ala Ser Thr Ser Val<br>305                    310                    315                    320 | 960 |
| act ttt aga gag atg gac atg agc ccg gag gaa gtg gtt gcc agc cct<br>Thr Phe Arg Glu Met Asp Met Ser Pro Glu Glu Val Val Ala Ser Pro<br>                    325                    330                    335 | 1008 |
| agg gcc tca cct gct aaa cag cgg ggt cct gag gca gcc tcc aat atc<br>Arg Ala Ser Pro Ala Lys Gln Arg Gly Pro Glu Ala Ala Ser Asn Ile<br>                        340                    345                    350 | 1056 |
| cag cag tgc ctc ttt ctc aag aag atg ggg gcc aaa ggc agc act cca<br>Gln Gln Cys Leu Phe Leu Lys Lys Met Gly Ala Lys Gly Ser Thr Pro<br>                  355                    360                    365 | 1104 |
| gga atg ttc aat ctt cca gtc agt ctc tac gtg acc agt caa ggt gaa<br>Gly Met Phe Asn Leu Pro Val Ser Leu Tyr Val Thr Ser Gln Gly Glu<br>        370                    375                    380 | 1152 |
| gta cta gtc gct gac cgt ggt aac tat cgt ata caa gtc ttt acc cgc<br>Val Leu Val Ala Asp Arg Gly Asn Tyr Arg Ile Gln Val Phe Thr Arg<br>385                    390                    395                    400 | 1200 |
| aaa ggc ttt ttg aag gaa atc cgc cgc agc ccc agt ggc att gat agc<br>Lys Gly Phe Leu Lys Glu Ile Arg Arg Ser Pro Ser Gly Ile Asp Ser<br>                    405                    410                    415 | 1248 |
| ttt gtg cta agc ttc ctt ggg gca gat cta ccc aac ctc act cct ctc<br>Phe Val Leu Ser Phe Leu Gly Ala Asp Leu Pro Asn Leu Thr Pro Leu<br>                  420                    425                    430 | 1296 |
| tca gtg gca atg aac tgc cag ggg ctg att ggt gtg act gac agc tat<br>Ser Val Ala Met Asn Cys Gln Gly Leu Ile Gly Val Thr Asp Ser Tyr<br>        435                    440                    445 | 1344 |
| gat aac tcc ctc aag gta tat acc ttg gat ggc cac tgc gtg gcc tgt<br>Asp Asn Ser Leu Lys Val Tyr Thr Leu Asp Gly His Cys Val Ala Cys<br>450                    455                    460 | 1392 |
| cac agg agc cag ctg agc aaa cca tgg ggt atc aca gcc ttg cca tct<br>His Arg Ser Gln Leu Ser Lys Pro Trp Gly Ile Thr Ala Leu Pro Ser<br>465                    470                    475                    480 | 1440 |
| ggc cag ttt gta gta acc gat gtg gaa ggt gga aag ctt tgg tgt ttc<br>Gly Gln Phe Val Val Thr Asp Val Glu Gly Gly Lys Leu Trp Cys Phe<br>                  485                    490                    495 | 1488 |
| aca gtt gat cga gga tca ggg gtg gtc aaa tac agc tgc cta tgt agt<br>Thr Val Asp Arg Gly Ser Gly Val Val Lys Tyr Ser Cys Leu Cys Ser<br>            500                    505                    510 | 1536 |

-continued

```
gct gtg cgg ccc aaa ttt gtc acc tgt gat gct gag ggc acc gtc tac     1584
Ala Val Arg Pro Lys Phe Val Thr Cys Asp Ala Glu Gly Thr Val Tyr
        515                 520                 525 ttc acc cag ggc tta ggc ctc aat ctg gag aat cgg cag aat gag cac     1632
Phe Thr Gln Gly Leu Gly Leu Asn Leu Glu Asn Arg Gln Asn Glu His
530                 535                 540 cac ctg gag ggt ggc ttt tcc att ggc tct gta ggc cct gat ggg cag     1680
His Leu Glu Gly Gly Phe Ser Ile Gly Ser Val Gly Pro Asp Gly Gln
545                 550                 555                 560 ctg ggt cgc cag att agc cac ttc ttc tcg gag aat gag gat ttc cgc     1728
Leu Gly Arg Gln Ile Ser His Phe Phe Ser Glu Asn Glu Asp Phe Arg
        565                 570                 575 tgc att gct ggc atg tgt gtg gat gct cgt ggt gat ctc atc gtg gct     1776
Cys Ile Ala Gly Met Cys Val Asp Ala Arg Gly Asp Leu Ile Val Ala
            580                 585                 590 gac agt agt cgc aag gaa att ctc cat ttt cct aag ggt ggg ggc tat     1824
Asp Ser Ser Arg Lys Glu Ile Leu His Phe Pro Lys Gly Gly Gly Tyr
    595                 600                 605 agt gtc ctt att cga gag gga ctt acc tgt ccg gtg ggc ata gcc cta     1872
Ser Val Leu Ile Arg Glu Gly Leu Thr Cys Pro Val Gly Ile Ala Leu
610                 615                 620 act cct aag ggg cag ctg ctg gtc ttg gac tgt tgg gat cat tgc atc     1920
Thr Pro Lys Gly Gln Leu Leu Val Leu Asp Cys Trp Asp His Cys Ile
625                 630                 635                 640 aag atc tac agc tac cat ctg aga aga tat tcc acc cca tag             1962
Lys Ile Tyr Ser Tyr His Leu Arg Arg Tyr Ser Thr Pro
            645                 650
```

<210> SEQ ID NO 2
<211> LENGTH: 653
<212> TYPE: PRT
<213> ORGANISM: Homo sapiens

<400> SEQUENCE: 2

```
Met Ala Ala Ala Ala Ser His Leu Asn Leu Asp Ala Leu Arg Glu
1               5                   10                  15

Val Leu Glu Cys Pro Ile Cys Met Glu Ser Phe Thr Glu Glu Gln Leu
                20                  25                  30

Arg Pro Lys Leu Leu His Cys Gly His Thr Ile Cys Arg Gln Cys Leu
            35                  40                  45

Glu Lys Leu Leu Ala Ser Ser Ile Asn Gly Val Arg Cys Pro Phe Cys
        50                  55                  60

Ser Lys Ile Thr Arg Ile Thr Ser Leu Thr Gln Leu Thr Asp Asn Leu
65                  70                  75                  80

Thr Val Leu Lys Ile Ile Asp Thr Ala Gly Leu Ser Glu Ala Val Gly
                85                  90                  95

Leu Leu Met Cys Arg Ser Cys Gly Arg Arg Leu Pro Arg Gln Phe Cys
            100                 105                 110

Arg Ser Cys Gly Leu Val Leu Cys Glu Pro Cys Arg Glu Ala Asp His
        115                 120                 125

Gln Pro Pro Gly His Cys Thr Leu Pro Val Lys Glu Ala Ala Glu Glu
    130                 135                 140

Arg Arg Arg Asp Phe Gly Glu Lys Leu Thr Arg Leu Arg Glu Leu Met
145                 150                 155                 160

Gly Glu Leu Gln Arg Arg Lys Ala Ala Leu Glu Gly Val Ser Lys Asp
                165                 170                 175

Leu Gln Ala Arg Tyr Lys Ala Val Leu Gln Glu Tyr Gly His Glu Glu
            180                 185                 190
```

```
-continued

Arg Arg Val Gln Asp Glu Leu Ala Arg Ser Arg Lys Phe Phe Thr Gly
        195                 200                 205

Ser Leu Ala Glu Val Glu Lys Ser Asn Ser Gln Val Val Glu Glu Gln
    210                 215                 220

Ser Tyr Leu Leu Asn Ile Ala Glu Val Gln Val Ser Arg Cys Asp
225                 230                 235                 240

Tyr Phe Leu Ala Lys Ile Lys Gln Ala Asp Val Ala Leu Leu Glu Glu
                245                 250                 255

Thr Ala Asp Glu Glu Pro Glu Leu Thr Ala Ser Leu Pro Arg Glu
            260                 265                 270

Leu Thr Leu Gln Asp Val Glu Leu Leu Lys Val Gly His Val Gly Pro
        275                 280                 285

Leu Gln Ile Gly Gln Ala Val Lys Lys Pro Arg Thr Val Asn Val Glu
        290                 295                 300

Asp Ser Trp Ala Met Glu Ala Thr Ala Ser Ala Ala Ser Thr Ser Val
305                 310                 315                 320

Thr Phe Arg Glu Met Asp Met Ser Pro Glu Glu Val Val Ala Ser Pro
                325                 330                 335

Arg Ala Ser Pro Ala Lys Gln Arg Gly Pro Glu Ala Ala Ser Asn Ile
            340                 345                 350

Gln Gln Cys Leu Phe Leu Lys Lys Met Gly Ala Lys Gly Ser Thr Pro
        355                 360                 365

Gly Met Phe Asn Leu Pro Val Ser Leu Tyr Val Thr Ser Gln Gly Glu
    370                 375                 380

Val Leu Val Ala Asp Arg Gly Asn Tyr Arg Ile Gln Val Phe Thr Arg
385                 390                 395                 400

Lys Gly Phe Leu Lys Glu Ile Arg Arg Ser Pro Ser Gly Ile Asp Ser
                405                 410                 415

Phe Val Leu Ser Phe Leu Gly Ala Asp Leu Pro Asn Leu Thr Pro Leu
            420                 425                 430

Ser Val Ala Met Asn Cys Gln Gly Leu Ile Gly Val Thr Asp Ser Tyr
        435                 440                 445

Asp Asn Ser Leu Lys Val Tyr Thr Leu Asp Gly His Cys Val Ala Cys
    450                 455                 460

His Arg Ser Gln Leu Ser Lys Pro Trp Gly Ile Thr Ala Leu Pro Ser
465                 470                 475                 480

Gly Gln Phe Val Val Thr Asp Val Glu Gly Gly Lys Leu Trp Cys Phe
                485                 490                 495

Thr Val Asp Arg Gly Ser Gly Val Val Lys Tyr Ser Cys Leu Cys Ser
            500                 505                 510

Ala Val Arg Pro Lys Phe Val Thr Cys Asp Ala Glu Gly Thr Val Tyr
        515                 520                 525

Phe Thr Gln Gly Leu Gly Leu Asn Leu Glu Asn Arg Gln Asn Glu His
    530                 535                 540

His Leu Glu Gly Gly Phe Ser Ile Gly Ser Val Gly Pro Asp Gly Gln
545                 550                 555                 560

Leu Gly Arg Gln Ile Ser His Phe Phe Ser Glu Asn Glu Asp Phe Arg
                565                 570                 575

Cys Ile Ala Gly Met Cys Val Asp Ala Arg Gly Asp Leu Ile Val Ala
            580                 585                 590

Asp Ser Ser Arg Lys Glu Ile Leu His Phe Pro Lys Gly Gly Gly Tyr
        595                 600                 605

Ser Val Leu Ile Arg Glu Gly Leu Thr Cys Pro Val Gly Ile Ala Leu
```

```
                610                 615                 620
Thr Pro Lys Gly Gln Leu Leu Val Leu Asp Cys Trp Asp His Cys Ile
625                 630                 635                 640

Lys Ile Tyr Ser Tyr His Leu Arg Arg Tyr Ser Thr Pro
                645                 650

<210> SEQ ID NO 3
<211> LENGTH: 2235
<212> TYPE: DNA
<213> ORGANISM: Homo sapiens
<220> FEATURE:
<221> NAME/KEY: CDS
<222> LOCATION: (1)..(2235)

<400> SEQUENCE: 3 atg gcc agt gaa ggc acc aac atc cca agt cct gtg gtg cgc cag att      48
Met Ala Ser Glu Gly Thr Asn Ile Pro Ser Pro Val Val Arg Gln Ile
1               5                   10                  15 gac aag cag ttt ctg att tgc agt ata tgc ctg gaa cgg tac aag aat      96
Asp Lys Gln Phe Leu Ile Cys Ser Ile Cys Leu Glu Arg Tyr Lys Asn
            20                  25                  30 ccc aag gtt ctc ccc tgt ctg cac act ttc tgc gag agg tgc ctg cag     144
Pro Lys Val Leu Pro Cys Leu His Thr Phe Cys Glu Arg Cys Leu Gln
        35                  40                  45 aac tac att cct gcc cac agt tta acc ctc tcc tgc cca gtg tgc cgc     192
Asn Tyr Ile Pro Ala His Ser Leu Thr Leu Ser Cys Pro Val Cys Arg
    50                  55                  60 cag acc tcc atc ctg ccc gag aaa ggg gtg gcc gcg ctc cag aac aat     240
Gln Thr Ser Ile Leu Pro Glu Lys Gly Val Ala Ala Leu Gln Asn Asn
65                  70                  75                  80 ttc ttc atc aca aac ctg atg gac gtg ctg cag cga act cca ggc agc     288
Phe Phe Ile Thr Asn Leu Met Asp Val Leu Gln Arg Thr Pro Gly Ser
                85                  90                  95 aac gct gag gag tct tcc atc ctg gag aca gtc act gct gtg gct gcg     336
Asn Ala Glu Glu Ser Ser Ile Leu Glu Thr Val Thr Ala Val Ala Ala
            100                 105                 110 gga aag cct ctc tct tgc cca aac cac gat ggg aat gtg atg gaa ttt     384
Gly Lys Pro Leu Ser Cys Pro Asn His Asp Gly Asn Val Met Glu Phe
        115                 120                 125 tac tgc cag tcc tgt gag act gcc atg tgt cgg gag tgc acg gag ggg     432
Tyr Cys Gln Ser Cys Glu Thr Ala Met Cys Arg Glu Cys Thr Glu Gly
    130                 135                 140 gag cac gca gag cac ccc aca gtt cca ctc aag gat gtg gtg gaa cag     480
Glu His Ala Glu His Pro Thr Val Pro Leu Lys Asp Val Val Glu Gln
145                 150                 155                 160 cac aag gcc tcg ctc cag gtc cag ctg gat gct gtc aac aaa agg ctc     528
His Lys Ala Ser Leu Gln Val Gln Leu Asp Ala Val Asn Lys Arg Leu
                165                 170                 175 cca gaa ata gat tct gct ctt cag ttc atc tct gaa atc att cat cag     576
Pro Glu Ile Asp Ser Ala Leu Gln Phe Ile Ser Glu Ile Ile His Gln
            180                 185                 190 tta acc aac caa aag gcc agc atc gtg gat gac att cat tcc acc ttt     624
Leu Thr Asn Gln Lys Ala Ser Ile Val Asp Asp Ile His Ser Thr Phe
        195                 200                 205 gat gag ctc cag aag act tta aat gtg cgc aag agt gtg ctg ctt atg     672
Asp Glu Leu Gln Lys Thr Leu Asn Val Arg Lys Ser Val Leu Leu Met
    210                 215                 220 gaa ttg gag gtc aac tat ggc ctc aaa cac aaa gtc ctc cag tcg cag     720
Glu Leu Glu Val Asn Tyr Gly Leu Lys His Lys Val Leu Gln Ser Gln
225                 230                 235                 240 ctg gat act ctg ctc cag ggg cag gag agc att aag agc tgc agc aac     768
```

```
                Leu Asp Thr Leu Leu Gln Gly Gln Glu Ser Ile Lys Ser Cys Ser Asn
                                245                 250                 255 ttc aca gcg cag gcc ctc aac cat ggc acg gag acc gag gtc cta ctg                816
Phe Thr Ala Gln Ala Leu Asn His Gly Thr Glu Thr Glu Val Leu Leu
                260                 265                 270 gtg aag aag cag atg agc gag aag ctg aac gag ctg gcc gac cag gac                864
Val Lys Lys Gln Met Ser Glu Lys Leu Asn Glu Leu Ala Asp Gln Asp
            275                 280                 285 ttc ccc ttg cac ccg cgg gag aac gac cag ctg gat ttc atc gtg gaa                912
Phe Pro Leu His Pro Arg Glu Asn Asp Gln Leu Asp Phe Ile Val Glu
        290                 295                 300 acc gag ggg ctg aag aag tcc atc cac aac ctc ggg acg atc tta acc                960
Thr Glu Gly Leu Lys Lys Ser Ile His Asn Leu Gly Thr Ile Leu Thr
305                 310                 315                 320 acc aac gcc gtt gcc tca gag aca gtg gcc acg ggc gag ggg ctg cgg               1008
Thr Asn Ala Val Ala Ser Glu Thr Val Ala Thr Gly Glu Gly Leu Arg
                325                 330                 335 cag acc atc atc ggg cag ccc atg tcc gtc acc atc acc acc aag gac               1056
Gln Thr Ile Ile Gly Gln Pro Met Ser Val Thr Ile Thr Thr Lys Asp
            340                 345                 350 aaa gac ggt gag ctg tgc aaa acc ggc aac gcc tac ctc acc gcc gaa               1104
Lys Asp Gly Glu Leu Cys Lys Thr Gly Asn Ala Tyr Leu Thr Ala Glu
        355                 360                 365 ctg agc acc ccc gac ggg agc gtg gca gac ggg gag atc ctg gac aac               1152
Leu Ser Thr Pro Asp Gly Ser Val Ala Asp Gly Glu Ile Leu Asp Asn
370                 375                 380 aag aac ggc acc tat gag ttt ttg tac act gtc cag aag gaa ggg gac               1200
Lys Asn Gly Thr Tyr Glu Phe Leu Tyr Thr Val Gln Lys Glu Gly Asp
385                 390                 395                 400 ttt acc ctg tct ctg aga ctc tat gac cag cac atc cga ggc agc ccg               1248
Phe Thr Leu Ser Leu Arg Leu Tyr Asp Gln His Ile Arg Gly Ser Pro
                405                 410                 415 ttt aag ctg aaa gtg atc cga tcc gct gat gtg tct ccc acc aca gaa               1296
Phe Lys Leu Lys Val Ile Arg Ser Ala Asp Val Ser Pro Thr Thr Glu
            420                 425                 430 ggc gtg aag agg cgc gtt aag tcc ccg ggg agc ggc cac gtc aag cag               1344
Gly Val Lys Arg Arg Val Lys Ser Pro Gly Ser Gly His Val Lys Gln
        435                 440                 445 aaa gct gtg aaa aga ccc gca agc atg tac agc act gga aaa cga aaa               1392
Lys Ala Val Lys Arg Pro Ala Ser Met Tyr Ser Thr Gly Lys Arg Lys
450                 455                 460 gag aat ccc atc gaa gac gat ttg atc ttt cga gtg ggt acc aaa gga               1440
Glu Asn Pro Ile Glu Asp Asp Leu Ile Phe Arg Val Gly Thr Lys Gly
465                 470                 475                 480 aga aat aaa gga gag ttt aca aat ctt cag ggg gta gct gca tct aca               1488
Arg Asn Lys Gly Glu Phe Thr Asn Leu Gln Gly Val Ala Ala Ser Thr
                485                 490                 495 aat gga aag ata tta att gca gac agt aac aac caa tgt gtg cag ata               1536
Asn Gly Lys Ile Leu Ile Ala Asp Ser Asn Asn Gln Cys Val Gln Ile
            500                 505                 510 ttt tcc aat gat ggc cag ttc aaa agt cgt ttt ggc ata cgg gga cgc               1584
Phe Ser Asn Asp Gly Gln Phe Lys Ser Arg Phe Gly Ile Arg Gly Arg
        515                 520                 525 tct ccg ggg cag ctg cag cgg ccc aca gga gtg gct gta cat ccc agt               1632
Ser Pro Gly Gln Leu Gln Arg Pro Thr Gly Val Ala Val His Pro Ser
530                 535                 540 ggg gac ata atc att gcc gat tat gat aat aaa tgg gtc agc att ttc               1680
Gly Asp Ile Ile Ile Ala Asp Tyr Asp Asn Lys Trp Val Ser Ile Phe
545                 550                 555                 560 tcc tcc gat ggg aaa ttt aag aca aaa att gga tca gga aag ctg atg               1728
```

|  |  |  |  |  |  |  |  |  |  |  |  |  |  |
|---|---|---|---|---|---|---|---|---|---|---|---|---|---|
| Ser | Ser | Asp | Gly | Lys | Phe | Lys | Thr | Lys | Ile | Gly | Ser | Gly | Lys | Leu | Met |
|  |  |  |  | 565 |  |  | 570 |  |  |  | 575 |

```
gga ccc aaa gga gtt tct gtg gac cgc aat ggg cac att att gtt gtg      1776
Gly Pro Lys Gly Val Ser Val Asp Arg Asn Gly His Ile Ile Val Val
            580                 585                 590 gac aac aag gcg tgc tgc gtg ttt atc ttc cag cca aac ggg aaa ata      1824
Asp Asn Lys Ala Cys Cys Val Phe Ile Phe Gln Pro Asn Gly Lys Ile
            595                 600                 605 gtc acc agg ttt ggt agc cga gga aat ggg gac agg cag ttt gca ggt      1872
Val Thr Arg Phe Gly Ser Arg Gly Asn Gly Asp Arg Gln Phe Ala Gly
            610                 615                 620 ccc cat ttt gca gct gta aat agc aat aat gag att att att aca gat      1920
Pro His Phe Ala Ala Val Asn Ser Asn Asn Glu Ile Ile Ile Thr Asp
625                 630                 635                 640 ttc cat aat cat tct gtc aag gtg ttt aat cag gaa gga gaa ttc atg      1968
Phe His Asn His Ser Val Lys Val Phe Asn Gln Glu Gly Glu Phe Met
                645                 650                 655 ttg aag ttt ggc tca aat gga gaa gga aat ggg cag ttt aat gct cca      2016
Leu Lys Phe Gly Ser Asn Gly Glu Gly Asn Gly Gln Phe Asn Ala Pro
            660                 665                 670 aca ggt gta gca gtg gat tca aat gga aac atc att gtg gcc gac tgg      2064
Thr Gly Val Ala Val Asp Ser Asn Gly Asn Ile Ile Val Ala Asp Trp
            675                 680                 685 gga aac agc agg atc cag gtt ttt gat ggg agt gga tca ttt ttg tcc      2112
Gly Asn Ser Arg Ile Gln Val Phe Asp Gly Ser Gly Ser Phe Leu Ser
    690                 695                 700 tac att aac aca tct gct gac cca ctc tat ggc ccc caa ggc ctg gcc      2160
Tyr Ile Asn Thr Ser Ala Asp Pro Leu Tyr Gly Pro Gln Gly Leu Ala
705                 710                 715                 720 cta act tca gat ggt cat gtt gtg gtt gca gac tct gga aat cac tgt      2208
Leu Thr Ser Asp Gly His Val Val Val Ala Asp Ser Gly Asn His Cys
                725                 730                 735 ttc aaa gtc tat cga tac tta cag taa                                  2235
Phe Lys Val Tyr Arg Tyr Leu Gln
            740
```

<210> SEQ ID NO 4
<211> LENGTH: 744
<212> TYPE: PRT
<213> ORGANISM: Homo sapiens

<400> SEQUENCE: 4

Met Ala Ser Glu Gly Thr Asn Ile Pro Ser Pro Val Val Arg Gln Ile
1               5                   10                  15

Asp Lys Gln Phe Leu Ile Cys Ser Ile Cys Leu Glu Arg Tyr Lys Asn
            20                  25                  30

Pro Lys Val Leu Pro Cys Leu His Thr Phe Cys Glu Arg Cys Leu Gln
        35                  40                  45

Asn Tyr Ile Pro Ala His Ser Leu Thr Leu Ser Cys Pro Val Cys Arg
    50                  55                  60

Gln Thr Ser Ile Leu Pro Glu Lys Gly Val Ala Ala Leu Gln Asn Asn
65                  70                  75                  80

Phe Phe Ile Thr Asn Leu Met Asp Val Leu Gln Arg Thr Pro Gly Ser
                85                  90                  95

Asn Ala Glu Glu Ser Ser Ile Leu Glu Thr Val Thr Ala Val Ala Ala
            100                 105                 110

Gly Lys Pro Leu Ser Cys Pro Asn His Asp Gly Asn Val Met Glu Phe
        115                 120                 125

Tyr Cys Gln Ser Cys Glu Thr Ala Met Cys Arg Glu Cys Thr Glu Gly

```
                    130                 135                 140
Glu His Ala Glu His Pro Thr Val Pro Leu Lys Asp Val Val Glu Gln
145                 150                 155                 160

His Lys Ala Ser Leu Gln Val Gln Leu Asp Ala Val Asn Lys Arg Leu
                    165                 170                 175

Pro Glu Ile Asp Ser Ala Leu Gln Phe Ile Ser Glu Ile Ile His Gln
                    180                 185                 190

Leu Thr Asn Gln Lys Ala Ser Ile Val Asp Asp Ile His Ser Thr Phe
                    195                 200                 205

Asp Glu Leu Gln Lys Thr Leu Asn Val Arg Lys Ser Val Leu Leu Met
210                 215                 220

Glu Leu Glu Val Asn Tyr Gly Leu Lys His Lys Val Leu Gln Ser Gln
225                 230                 235                 240

Leu Asp Thr Leu Leu Gln Gly Gln Glu Ser Ile Lys Ser Cys Ser Asn
                    245                 250                 255

Phe Thr Ala Gln Ala Leu Asn His Gly Thr Glu Thr Glu Val Leu Leu
                    260                 265                 270

Val Lys Lys Gln Met Ser Glu Lys Leu Asn Glu Leu Ala Asp Gln Asp
                    275                 280                 285

Phe Pro Leu His Pro Arg Glu Asn Asp Gln Leu Asp Phe Ile Val Glu
290                 295                 300

Thr Glu Gly Leu Lys Lys Ser Ile His Asn Leu Gly Thr Ile Leu Thr
305                 310                 315                 320

Thr Asn Ala Val Ala Ser Glu Thr Val Ala Thr Gly Glu Gly Leu Arg
                    325                 330                 335

Gln Thr Ile Ile Gly Gln Pro Met Ser Val Thr Ile Thr Thr Lys Asp
                    340                 345                 350

Lys Asp Gly Glu Leu Cys Lys Thr Gly Asn Ala Tyr Leu Thr Ala Glu
                    355                 360                 365

Leu Ser Thr Pro Asp Gly Ser Val Ala Asp Gly Glu Ile Leu Asp Asn
                    370                 375                 380

Lys Asn Gly Thr Tyr Glu Phe Leu Tyr Thr Val Gln Lys Glu Gly Asp
385                 390                 395                 400

Phe Thr Leu Ser Leu Arg Leu Tyr Asp Gln His Ile Arg Gly Ser Pro
                    405                 410                 415

Phe Lys Leu Lys Val Ile Arg Ser Ala Asp Val Ser Pro Thr Thr Glu
                    420                 425                 430

Gly Val Lys Arg Val Lys Ser Pro Gly Ser Gly His Val Lys Gln
                    435                 440                 445

Lys Ala Val Lys Arg Pro Ala Ser Met Tyr Ser Thr Gly Lys Arg Lys
450                 455                 460

Glu Asn Pro Ile Glu Asp Asp Leu Ile Phe Arg Val Gly Thr Lys Gly
465                 470                 475                 480

Arg Asn Lys Gly Glu Phe Thr Asn Leu Gln Gly Val Ala Ala Ser Thr
                    485                 490                 495

Asn Gly Lys Ile Leu Ile Ala Asp Ser Asn Asn Gln Cys Val Gln Ile
                    500                 505                 510

Phe Ser Asn Asp Gly Gln Phe Lys Ser Arg Phe Gly Ile Arg Gly Arg
                    515                 520                 525

Ser Pro Gly Gln Leu Gln Arg Pro Thr Gly Val Ala Val His Pro Ser
                    530                 535                 540

Gly Asp Ile Ile Ile Ala Asp Tyr Asp Asn Lys Trp Val Ser Ile Phe
545                 550                 555                 560
```

-continued

```
Ser Ser Asp Gly Lys Phe Lys Thr Lys Ile Gly Ser Gly Lys Leu Met
            565                 570                 575
Gly Pro Lys Gly Val Ser Val Asp Arg Asn Gly His Ile Ile Val Val
            580                 585                 590
Asp Asn Lys Ala Cys Cys Val Phe Ile Phe Gln Pro Asn Gly Lys Ile
            595                 600                 605
Val Thr Arg Phe Gly Ser Arg Gly Asn Gly Asp Arg Gln Phe Ala Gly
            610                 615                 620
Pro His Phe Ala Ala Val Asn Ser Asn Asn Glu Ile Ile Thr Asp
625                 630                 635                 640
Phe His Asn His Ser Val Lys Val Phe Asn Gln Glu Gly Glu Phe Met
            645                 650                 655
Leu Lys Phe Gly Ser Asn Gly Glu Gly Asn Gly Gln Phe Asn Ala Pro
            660                 665                 670
Thr Gly Val Ala Val Asp Ser Asn Gly Asn Ile Ile Val Ala Asp Trp
            675                 680                 685
Gly Asn Ser Arg Ile Gln Val Phe Asp Gly Ser Gly Ser Phe Leu Ser
            690                 695                 700
Tyr Ile Asn Thr Ser Ala Asp Pro Leu Tyr Gly Pro Gln Gly Leu Ala
705                 710                 715                 720
Leu Thr Ser Asp Gly His Val Val Ala Asp Ser Gly Asn His Cys
            725                 730                 735
Phe Lys Val Tyr Arg Tyr Leu Gln
            740

<210> SEQ ID NO 5
<211> LENGTH: 2235
<212> TYPE: DNA
<213> ORGANISM: Homo sapiens
<220> FEATURE:
<221> NAME/KEY: CDS
<222> LOCATION: (1)..(2235)

<400> SEQUENCE: 5 atg gca aag agg gag gac agc cct ggc cca gag gtc cag cca atg gac    48
Met Ala Lys Arg Glu Asp Ser Pro Gly Pro Glu Val Gln Pro Met Asp
1               5                   10                  15 aag cag ttc ctg gta tgc agc atc tgc ctg gat cgg tac cag tgc ccc    96
Lys Gln Phe Leu Val Cys Ser Ile Cys Leu Asp Arg Tyr Gln Cys Pro
                20                  25                  30 aag gtt ctt cct tgc ctg cac acc ttc tgt gag aga tgt ctc caa aac    144
Lys Val Leu Pro Cys Leu His Thr Phe Cys Glu Arg Cys Leu Gln Asn
            35                  40                  45 tat atc cct gcc cag agc ctg acg cta tcc tgt cca gta tgc cgg cag    192
Tyr Ile Pro Ala Gln Ser Leu Thr Leu Ser Cys Pro Val Cys Arg Gln
        50                  55                  60 acg tcc atc ctc cca gag cag ggc gtc tcg gca ctg cag aac aac ttc    240
Thr Ser Ile Leu Pro Glu Gln Gly Val Ser Ala Leu Gln Asn Asn Phe
65                  70                  75                  80 ttc atc agc agc ctc atg gag gca atg cag cag gca cct gat ggg gcc    288
Phe Ile Ser Ser Leu Met Glu Ala Met Gln Gln Ala Pro Asp Gly Ala
                85                  90                  95 cac gac ccg gag gac ccc cac ccc ctc agt gta gtg gct ggc cgc cct    336
His Asp Pro Glu Asp Pro His Pro Leu Ser Val Val Ala Gly Arg Pro
                100                 105                 110 ctc tcc tgc ccc aac cat gaa ggc aag acg atg gag ttt tac tgt gag    384
Leu Ser Cys Pro Asn His Glu Gly Lys Thr Met Glu Phe Tyr Cys Glu
            115                 120                 125 gcc tgt gag acg gcc atg tgt ggt gag tgc cgc gcc ggg gag cat cgt    432
```

```
        Ala Cys Glu Thr Ala Met Cys Gly Glu Cys Arg Ala Gly Glu His Arg
            130                 135                 140 gag cat ggc aca gtg ctg ctg agg gat gtg gtg gag cag cac aag gcg       480
Glu His Gly Thr Val Leu Leu Arg Asp Val Val Glu Gln His Lys Ala
145                 150                 155                 160 gcc ctg cag cgc cag ctc gag gct gtg cgt ggc cga ttg cca cag ctg       528
Ala Leu Gln Arg Gln Leu Glu Ala Val Arg Gly Arg Leu Pro Gln Leu
                165                 170                 175 tcc gca gca att gcc tta gtc ggg ggc atc agc cag cag ctg cag gag       576
Ser Ala Ala Ile Ala Leu Val Gly Gly Ile Ser Gln Gln Leu Gln Glu
            180                 185                 190 cgc aag gca gag gcc ctg gcc cag atc agt gca gcg ttc gag gac ctg       624
Arg Lys Ala Glu Ala Leu Ala Gln Ile Ser Ala Ala Phe Glu Asp Leu
        195                 200                 205 gag caa gca ctg cag cag cgc aag cag gct ctg gtc agc gac ctg gag       672
Glu Gln Ala Leu Gln Gln Arg Lys Gln Ala Leu Val Ser Asp Leu Glu
    210                 215                 220 acc att tgt ggg gcc aaa cag aag gtg ttg caa agc cag ctg gac aca       720
Thr Ile Cys Gly Ala Lys Gln Lys Val Leu Gln Ser Gln Leu Asp Thr
225                 230                 235                 240 ctg cgc cag ggt cag gaa cac atc ggc agt agc tgc agc ttt gca gag       768
Leu Arg Gln Gly Gln Glu His Ile Gly Ser Ser Cys Ser Phe Ala Glu
                245                 250                 255 cag gca ctg cgc ctg ggc tcg gcc ccg gag gtg ttg ctg gtg cgc aag       816
Gln Ala Leu Arg Leu Gly Ser Ala Pro Glu Val Leu Leu Val Arg Lys
            260                 265                 270 cac atg cga gag cgg ctg gct gca ttg gcg gca cag gcc ttc ccg gag       864
His Met Arg Glu Arg Leu Ala Ala Leu Ala Ala Gln Ala Phe Pro Glu
        275                 280                 285 cgg cca cat gag aat gca cag ctg gaa ctg gtc ctt gag gtg gac ggt       912
Arg Pro His Glu Asn Ala Gln Leu Glu Leu Val Leu Glu Val Asp Gly
    290                 295                 300 ctg cgg cga tcg gtg ctc aat ctg ggc gca ctg ctc acc acg agc gcc       960
Leu Arg Arg Ser Val Leu Asn Leu Gly Ala Leu Leu Thr Thr Ser Ala
305                 310                 315                 320 act gca cac gaa acg gtg gcc acg gga gag ggc ctg cgc cag gcg cta      1008
Thr Ala His Glu Thr Val Ala Thr Gly Glu Gly Leu Arg Gln Ala Leu
                325                 330                 335 gtg ggc cag cct gcc tcg ctc act gtc act acc aaa gac aag gac ggg      1056
Val Gly Gln Pro Ala Ser Leu Thr Val Thr Thr Lys Asp Lys Asp Gly
            340                 345                 350 cgg ttg gtg cgc aca ggc agc gct gag ctg cgt gca gag atc acc ggc      1104
Arg Leu Val Arg Thr Gly Ser Ala Glu Leu Arg Ala Glu Ile Thr Gly
        355                 360                 365 ccg gac ggc acg cgc ctt ccg gtg cca gtg gtg gac cac aag aat ggc      1152
Pro Asp Gly Thr Arg Leu Pro Val Pro Val Val Asp His Lys Asn Gly
    370                 375                 380 aca tat gag cta gtg tac aca gcg cgc acg gaa ggc gag ctg ctc ctc      1200
Thr Tyr Glu Leu Val Tyr Thr Ala Arg Thr Glu Gly Glu Leu Leu Leu
385                 390                 395                 400 tcg gtg ctg ctc tac gga cag cca gtg cgc ggc agc ccc ttc cgc gtg      1248
Ser Val Leu Leu Tyr Gly Gln Pro Val Arg Gly Ser Pro Phe Arg Val
                405                 410                 415 cgt gcc ctg cgt ccg ggg gac ctg cca cct tcc ccg gac gat gtg aag      1296
Arg Ala Leu Arg Pro Gly Asp Leu Pro Pro Ser Pro Asp Asp Val Lys
            420                 425                 430 cgc cgt gtc aag tcc cct ggc ggc ccc ggc agc cat gtg cgc cag aag      1344
Arg Arg Val Lys Ser Pro Gly Gly Pro Gly Ser His Val Arg Gln Lys
        435                 440                 445 gca gtg cgt agg ccc agc tcc atg tac agc aca ggc ggc aaa cga aag      1392
```

-continued

| | | |
|---|---|---|
| Ala Val Arg Arg Pro Ser Ser Met Tyr Ser Thr Gly Gly Lys Arg Lys<br>450 455 460 | | |
| gac aac cca att gag gat gag ctc gtc ttc cgt gtt ggc agt cgt gga<br>Asp Asn Pro Ile Glu Asp Glu Leu Val Phe Arg Val Gly Ser Arg Gly<br>465 470 475 480 | 1440 | |
| agg gag aaa ggt gaa ttc acc aat tta caa ggt gtg tcc gca gcc agc<br>Arg Glu Lys Gly Glu Phe Thr Asn Leu Gln Gly Val Ser Ala Ala Ser<br>485 490 495 | 1488 | |
| agc ggc cgc atc gtg gta gca gac agc aac aac cag tgt att cag gtt<br>Ser Gly Arg Ile Val Val Ala Asp Ser Asn Asn Gln Cys Ile Gln Val<br>500 505 510 | 1536 | |
| ttc tcc aat gag ggc cag ttc aag ttc cgt ttt ggg gtc cga gga cgc<br>Phe Ser Asn Glu Gly Gln Phe Lys Phe Arg Phe Gly Val Arg Gly Arg<br>515 520 525 | 1584 | |
| tca cct ggg cag ctg cag cgc ccc aca ggt gtg gca gtg gac acc aat<br>Ser Pro Gly Gln Leu Gln Arg Pro Thr Gly Val Ala Val Asp Thr Asn<br>530 535 540 | 1632 | |
| gga gac ata att gtg gca gac tat gac aac cgt tgg gtc agc atc ttc<br>Gly Asp Ile Ile Val Ala Asp Tyr Asp Asn Arg Trp Val Ser Ile Phe<br>545 550 555 560 | 1680 | |
| tcc cct gag ggc aag ttc aag acc aag att gga gct ggc cgc ctc atg<br>Ser Pro Glu Gly Lys Phe Lys Thr Lys Ile Gly Ala Gly Arg Leu Met<br>565 570 575 | 1728 | |
| ggc ccc aag gga gtg gcc gta gac cgg aat gga cat atc att gtg gtc<br>Gly Pro Lys Gly Val Ala Val Asp Arg Asn Gly His Ile Ile Val Val<br>580 585 590 | 1776 | |
| gac aac aag tct tgc tgc gtc ttt acc ttc cag ccc aat ggc aaa ctg<br>Asp Asn Lys Ser Cys Cys Val Phe Thr Phe Gln Pro Asn Gly Lys Leu<br>595 600 605 | 1824 | |
| gtt ggc cgt ttt ggg ggc cgt ggg gcc act gac cgc cac ttt gca ggg<br>Val Gly Arg Phe Gly Gly Arg Gly Ala Thr Asp Arg His Phe Ala Gly<br>610 615 620 | 1872 | |
| ccc cat ttt gtg gct gtg aac aac aag aat gaa att gta gta acg gac<br>Pro His Phe Val Ala Val Asn Asn Lys Asn Glu Ile Val Val Thr Asp<br>625 630 635 640 | 1920 | |
| ttc cat aac cat tca gtg aag gtg tac agt gcc gat gga gag ttc ctc<br>Phe His Asn His Ser Val Lys Val Tyr Ser Ala Asp Gly Glu Phe Leu<br>645 650 655 | 1968 | |
| ttc aag ttt ggc tcc cat ggc gag ggc aat ggg cag ttc aat gcc ccc<br>Phe Lys Phe Gly Ser His Gly Glu Gly Asn Gly Gln Phe Asn Ala Pro<br>660 665 670 | 2016 | |
| aca gga gta gct gtg gac tcc aat gga aac atc att gtg gct gac tgg<br>Thr Gly Val Ala Val Asp Ser Asn Gly Asn Ile Ile Val Ala Asp Trp<br>675 680 685 | 2064 | |
| ggc aac agc cgc atc cag gta ttc gac agc tct ggc tcc ttc ctg tcc<br>Gly Asn Ser Arg Ile Gln Val Phe Asp Ser Ser Gly Ser Phe Leu Ser<br>690 695 700 | 2112 | |
| tat atc aac aca tct gca gaa cca ctg tat ggt cca cag ggc ctg gca<br>Tyr Ile Asn Thr Ser Ala Glu Pro Leu Tyr Gly Pro Gln Gly Leu Ala<br>705 710 715 720 | 2160 | |
| ctg acc tcg gat ggc cat gtg gtg gtg gct gat gct ggc aac cac tgc<br>Leu Thr Ser Asp Gly His Val Val Val Ala Asp Ala Gly Asn His Cys<br>725 730 735 | 2208 | |
| ttt aaa gcc tat cgc tac ctc cag tag<br>Phe Lys Ala Tyr Arg Tyr Leu Gln<br>740 | 2235 | |

<210> SEQ ID NO 6
<211> LENGTH: 744
<212> TYPE: PRT
<213> ORGANISM: Homo sapiens

<400> SEQUENCE: 6

```
Met Ala Lys Arg Glu Asp Ser Pro Gly Pro Glu Val Gln Pro Met Asp
1               5                   10                  15

Lys Gln Phe Leu Val Cys Ser Ile Cys Leu Asp Arg Tyr Gln Cys Pro
            20                  25                  30

Lys Val Leu Pro Cys Leu His Thr Phe Cys Glu Arg Cys Leu Gln Asn
        35                  40                  45

Tyr Ile Pro Ala Gln Ser Leu Thr Leu Ser Cys Pro Val Cys Arg Gln
50                  55                  60

Thr Ser Ile Leu Pro Glu Gln Gly Val Ser Ala Leu Gln Asn Asn Phe
65                  70                  75                  80

Phe Ile Ser Ser Leu Met Glu Ala Met Gln Gln Ala Pro Asp Gly Ala
                85                  90                  95

His Asp Pro Glu Asp Pro His Pro Leu Ser Val Val Ala Gly Arg Pro
            100                 105                 110

Leu Ser Cys Pro Asn His Glu Gly Lys Thr Met Glu Phe Tyr Cys Glu
        115                 120                 125

Ala Cys Glu Thr Ala Met Cys Gly Glu Cys Arg Ala Gly Glu His Arg
130                 135                 140

Glu His Gly Thr Val Leu Leu Arg Asp Val Val Glu Gln His Lys Ala
145                 150                 155                 160

Ala Leu Gln Arg Gln Leu Glu Ala Val Arg Gly Arg Leu Pro Gln Leu
                165                 170                 175

Ser Ala Ala Ile Ala Leu Val Gly Gly Ile Ser Gln Gln Leu Gln Glu
            180                 185                 190

Arg Lys Ala Glu Ala Leu Ala Gln Ile Ser Ala Ala Phe Glu Asp Leu
        195                 200                 205

Glu Gln Ala Leu Gln Gln Arg Lys Gln Ala Leu Val Ser Asp Leu Glu
210                 215                 220

Thr Ile Cys Gly Ala Lys Gln Lys Val Leu Gln Ser Gln Leu Asp Thr
225                 230                 235                 240

Leu Arg Gln Gly Gln Glu His Ile Gly Ser Ser Cys Ser Phe Ala Glu
                245                 250                 255

Gln Ala Leu Arg Leu Gly Ser Ala Pro Glu Val Leu Leu Val Arg Lys
            260                 265                 270

His Met Arg Glu Arg Leu Ala Ala Leu Ala Ala Gln Ala Phe Pro Glu
        275                 280                 285

Arg Pro His Glu Asn Ala Gln Leu Glu Leu Val Leu Glu Val Asp Gly
290                 295                 300

Leu Arg Arg Ser Val Leu Asn Leu Gly Ala Leu Leu Thr Thr Ser Ala
305                 310                 315                 320

Thr Ala His Glu Thr Val Ala Thr Gly Glu Gly Leu Arg Gln Ala Leu
                325                 330                 335

Val Gly Gln Pro Ala Ser Leu Thr Val Thr Lys Asp Lys Asp Gly
            340                 345                 350

Arg Leu Val Arg Thr Gly Ser Ala Glu Leu Arg Ala Glu Ile Thr Gly
        355                 360                 365

Pro Asp Gly Thr Arg Leu Pro Val Pro Val Asp His Lys Asn Gly
370                 375                 380

Thr Tyr Glu Leu Val Tyr Thr Ala Arg Thr Glu Gly Glu Leu Leu Leu
385                 390                 395                 400

Ser Val Leu Leu Tyr Gly Gln Pro Val Arg Gly Ser Pro Phe Arg Val
                405                 410                 415
```

```
Arg Ala Leu Arg Pro Gly Asp Leu Pro Pro Ser Pro Asp Asp Val Lys
            420                 425                 430
Arg Arg Val Lys Ser Pro Gly Pro Gly Ser His Val Arg Gln Lys
        435                 440                 445
Ala Val Arg Arg Pro Ser Ser Met Tyr Ser Thr Gly Gly Lys Arg Lys
450                 455                 460
Asp Asn Pro Ile Glu Asp Glu Leu Val Phe Arg Val Gly Ser Arg Gly
465                 470                 475                 480
Arg Glu Lys Gly Glu Phe Thr Asn Leu Gln Gly Val Ser Ala Ala Ser
                485                 490                 495
Ser Gly Arg Ile Val Val Ala Asp Ser Asn Asn Gln Cys Ile Gln Val
            500                 505                 510
Phe Ser Asn Glu Gly Gln Phe Lys Phe Arg Phe Gly Val Arg Gly Arg
        515                 520                 525
Ser Pro Gly Gln Leu Gln Arg Pro Thr Gly Val Ala Val Asp Thr Asn
530                 535                 540
Gly Asp Ile Ile Val Ala Asp Tyr Asp Asn Arg Trp Val Ser Ile Phe
545                 550                 555                 560
Ser Pro Glu Gly Lys Phe Lys Thr Lys Ile Gly Ala Gly Arg Leu Met
                565                 570                 575
Gly Pro Lys Gly Val Ala Val Asp Arg Asn Gly His Ile Ile Val Val
            580                 585                 590
Asp Asn Lys Ser Cys Cys Val Phe Thr Phe Gln Pro Asn Gly Lys Leu
        595                 600                 605
Val Gly Arg Phe Gly Gly Arg Gly Ala Thr Asp Arg His Phe Ala Gly
610                 615                 620
Pro His Phe Val Ala Val Asn Asn Lys Asn Glu Ile Val Val Thr Asp
625                 630                 635                 640
Phe His Asn His Ser Val Lys Val Tyr Ser Ala Asp Gly Glu Phe Leu
                645                 650                 655
Phe Lys Phe Gly Ser His Gly Glu Gly Asn Gly Gln Phe Asn Ala Pro
            660                 665                 670
Thr Gly Val Ala Val Asp Ser Asn Gly Asn Ile Ile Val Ala Asp Trp
        675                 680                 685
Gly Asn Ser Arg Ile Gln Val Phe Asp Ser Ser Gly Ser Phe Leu Ser
690                 695                 700
Tyr Ile Asn Thr Ser Ala Glu Pro Leu Tyr Gly Pro Gln Gly Leu Ala
705                 710                 715                 720
Leu Thr Ser Asp Gly His Val Val Ala Asp Ala Gly Asn His Cys
                725                 730                 735
Phe Lys Ala Tyr Arg Tyr Leu Gln
            740

<210> SEQ ID NO 7
<211> LENGTH: 19
<212> TYPE: DNA
<213> ORGANISM: Artificial
<220> FEATURE:
<223> OTHER INFORMATION: Synthetic primer

<400> SEQUENCE: 7
gatcttcagg caaggtata                                                    19
```

METHODS FOR MODULATING THE PROLIFERATION AND DIFFERENTIATION POTENTIAL OF STEM CELLS AND PROGENITOR CELLS

This application is a national phase application under 35 U.S.C. §371 of International Application No. PCT/EP2008/062568 filed 19 Sep. 2008, which claims priority to European Application No. 07117501.2 filed 28 Sep. 2007. The entire text of each of the above-referenced disclosures is specifically incorporated herein by reference without disclaimer.

The present invention relates to the proliferation and differentiation of stem cells and progenitor cells.

Stem cells are pluripotent cells defined by their ability to self renew and the capacity to differentiate into any mature cell type.

Progenitor cells are early descendants of stem cells that can differentiate, but have a limited capacity for self-renewal cannot renew themselves anymore. A progenitor cell is multipotent, i.e. has a reduced potential than a stem cell with regard to the cell types into which it can differentiate.

Embryonic stem cells are cells that can differentiate into all cell types, they are derived from the inner cell mass of a blastocyst, an early stage embryo. In numerous tissues, stem cells persist throughout adult life; these stem cells are termed "adult stem cells" or "somatic stem cells". Adult stem cells, in contrast to embryonic stem cells, have a less versatile potential; therefore, they are sometimes defined as progenitor cells, not as stem cells.

The primary roles of adult stem cells, including neural stem cells, are to maintain and repair the tissue in which they are present, e.g. to replace the mature cells that are lost due to turnover, injury, or disease. However, the regenerative power of stem cells declines with age. As a consequence, aging tissues exhibit reduced repair capacity and an increased susceptibility for degenerative disease.

The properties of multipotent stem cells, e.g. neural stem cells (NSCs), in particular the ability to repair the tissues in which they are located, holds great promise in the development of novel therapies for the treatment of chronic and degenerative diseases, e.g. cell replacement therapies or direct administration of drugs that promote the potency of adult stem cells in situ.

Especially, such therapies in diseases like Parkinson's disease, Alzheimer's disease or after stroke (neuronal replacement) or diabetes, heart disease or leukemia, are considered to be very promising. In neurodegenerative diseases, one of the concepts of regenerative approaches is the replacement of died neurons with NSCs in the diseased brain. The NSCs eventually differentiate into postmitotic neurons, integrate in the neuronal network and thereby compensate for the disease-induced loss of neurons.

Hence, there is a need for agents that have the ability to control the proliferation of stem cells, both in vitro and in vivo. Therefore, it is an object of the invention to explore the mechanisms of stem cell proliferation and to identify proteins that are causally involved in these mechanisms.

In the experiments of the invention, it has surprisingly been found, by means of TRIM32, that members of the TRIM-NHL protein family are key players in stem cell differentiation. The findings of the present invention about the role TRIM-NHL proteins in stem cell differentiation provide the basis for identifying and using compounds that are able to regulate proliferation and/or differentiation of stem cells.

The defining feature of the TRIM-NHL protein family is a special domain organization, the so called tripartite motif (TRIM). This motif consists of a RING domain (TRIM2: aa position 23 to aa position 66; TRIM3: aa position 22 to aa position 65; TRIM32: aa position 21 to aa position 65), a B-Box and a coiled-coil region. In addition to these domains, TRIM32 (GenBank Accession Nos. NM_012210 and NM_053084) TRIM2 (GenBank Accession No. NM_015271) and TRIM3 (GenBank Accession No. NM_033278) have a large C-terminal NHL domain (TRIM2: aa position 490 to aa position 735; TRIM3: aa position 481 to aa position 741; TRIM32: aa position 446 to aa position 646; the acronym NHL derives from three of the founding members of the protein family; i.e. NCL-1, HT2A, and LIN-41).

In the meaning of the present invention, in addition to TRIM2, TRIM3 and TRIM32, other proteins containing a domain architecture that comprises the NHL domain as well as a B-Box and a coiled-coil region, are collectively referred to as "TRIM-NHL" proteins. An example for such other TRIM-NHL protein is LIN41 (GenBank Accession No. DQ232881).

Very little is known about the biological and molecular mechanisms mediated by the TRIM-NHL genes. The RING domain strongly suggests that TRIM32 is an E3-ubiquitin ligase and therefore mediates ubiquitination and degradation of certain target proteins. So far, TRIM32 has been mainly described to be involved in muscular dystrophy and Bardet-Biedl syndrome (BBS) (Chiang et al., 2006; Kudryashova et al., 2005). It has been shown that TRIM32 can act as a ubiquitin ligase for the Proteins Actin and Piasy (Kudryashova et al., 2005; Albor et al., 2006). Furthermore a recent study showed that TRIM32 is deregulated in the brains of Alzheimer's disease patients (Yokota et al., 2006). So far, TRIM32 has not been studied in the context of stem cell proliferation and differentiation.

To see whether TRIM32 is expressed in neural stem cells, an anti-TRIM32 antibody was raised. This antibody was used for immunofluorescence stainings of mouse brain sections (embryonic days 12.5 to 18.5). A positive staining was obtained in the ventricular zone (the region where the neural stem cells are localized) and the cortical plate (the region where postmitoric neurons are localized). Specificity of the antibody was demonstrated via preincubation of the antibody with the peptide that had been used for generation of that antibody. After such peptide block, no specific TRIM32 could be detected. Furthermore, the TRIM32 signal co-localized with Nestin staining Nestin is specifically expressed in neural stem cells, therefore the anti-Nestin antibody is widely used as a neural stem cell marker. A positive TRIM32 signal could also be detected in permanent cultures of neural stem cells and postmitotic neurons in vitro. From these results, it can be concluded that TRIM32 is expressed in neural stem cells in vivo and in vitro. In order to generate neurons, neural stem cells can divide asymmetrically. In such a neurogenic cell division the more apical daughter cell retains the stem cell characteristics, while the more basal daughter cell leaves the cell cycle and becomes a postmitotic neuron. In these cell divisions, TRIM32 is usually enriched in the basal daughter cell and is therefore asymmetrically segregated in the cell that will become a neuron.

To investigate the effect of TRIM32 enrichment, the inventors over-expressed TRIM32 in NIH3T3, neuroblastoma cells (N2a), colon carcinoma cells (CT26)) and primary neural stem cells. It has been found that in any of these cell types an expression of TRIM32 leads to an inhibition of proliferation (relative to control cells that just have been transfected with an expression vector for Enhanced Green Fluorescent Protein (EGFP). Proliferation was measured through immunofluorescence stainings with the proliferation antigen Ki67 and the mitotic marker P-H3. For primary neural stem cells, proliferation was also measured through the size of a colony that can be formed by a single transfected cell in a certain time. Also here the colony size for EGFP-TRIM32 transfected cells was found to be much smaller than for EGFP transfected cells. Furthermore, a knock-down of TRIM32, via transfection of an expression vector for short-hairpin RNA against TRIM32, was shown to promote proliferation of these cells. Also in this assay, proliferation was measured through immunofluorescence staining with the proliferation antigen Ki67 and the mitotic marker P-H3.

Proliferation and differentiation are tightly coupled processes. Therefore, the inventors investigated how expression or knock-down of TRIM32 affects the differentiation of neural stem cells. To measure the differentiation status of a neural stem cell, different markers were used, i.e. Nestin as a marker for neural stem cells and TuJ1 and MAP2 as markers for differentiated neurons. When TRIM32 was expressed in neural stem cells, the majority of these cells became positive for MAP2 and TuJ1, indicating that they differentiate into neurons. In contrast to this, after a knock-down of TRIM32, the neural stem cells stayed nestin positive, they did not differentiate into neurons. Furthermore, the neural stem cells that were transfected with a knock-down construct for TRIM32 did not even differentiate into neurons when they are exposed to culture conditions (withdrawal of the growth factor EGF) under which control neural stem cells (transfected with an control small hairpin RNA (shRNA) vector that targets no gene) easily differentiate into postmitotic neurons.

In addition, the inventors could show that overexpression of TRIM2 and TRIM3 in fibroblasts results in an inhibition of cell proliferation, suggesting that these TRIM-NHL proteins have a similar potential as TRIM32. To confirm the results for stem cells and to determine such properties for other TRIM-NHL proteins, e.g. LIN41, the experiments described in the Examples for TRIM32 (overexpression or inhibition, respectively, in neural stem cells) can be conducted in an analogous or similar way (e.g. extending the experiments to other stem cells) for TRIM2, TRIM3 and other TRIM-NHL proteins like LIN41.

These results provide evidence that the activity of a TRIM-NHL protein selected from TRIM2, TRIM3 or TRIM32, results in a stop of proliferation and an enhancement of differentiation, while the absence of TRIM-NHL promotes proliferation and inhibits differentiation.

In a first aspect, the present invention relates to a method for modulating the proliferation and/or differentiation potential of progenitor cells or stem cells, comprising modulating in said cells the level of expression and/or activity of a protein from the TRIM-NHL protein family, wherein said protein is selected from TRIM32 (SEQ ID NO:2), TRIM2 (SEQ ID NO:4) or TRIM3 (SEQ ID NO:6).

The term "modulating the level of expression and/or activity of a protein from the TRIM-NHL protein family" also encompasses modulating the expression/activity of more than one TRIM-NHL proteins, e.g. by an agent that is not strictly specific for one TRIM-NHL protein, but has an inhibiting or activating effect on more than one TRIM-NHL proteins.

In certain aspects, the method of the invention comprises decreasing the level of expression and/or activity of a TRIM-NHL protein selected from TRIM2, TRIM3 or TRIM32 in stem cells, thereby inhibiting the differentiation potential and promoting the proliferation potential of said stem cells.

For simplicity, if not otherwise indicated, in the following, the term "stem cells" also encompasses multipotent progenitor cells, both in general and with regard to specific stem cells and the progenitor cells derived therefrom.

For simplicity, in the following, reference to TRIM32 also includes reference to TRIM2 TRIM3 or other TRIM-NHL proteins, if not otherwise indicated. Also, the term "TRIM-NHL protein", stands for a protein selected from TRIM2, TRIM3, TRIM32 or any other TRIM-NHL protein.

Inhibiting the differentiation potential and promoting the proliferation potential of stem cells, i.e. keeping the cells in an undifferentiated state, is also understood as "maintenance of stem cells".

In specific embodiments, the method of the invention is an in vitro method for maintenance of stem cells. In such method, stem cells are kept in a stem cell medium that contains an inhibitor of one or more TRIM-NHL proteins, e.g. a TRIM32 inhibitor. Such inhibitor may be a nucleotide-type inhibitor or a compound identified and/or optimized in the assay methods of the invention, as described below, in particular, a small chemical compound. Stem cells and progenitor cells treated with a TRIM-NHL protein inhibitor are useful for transplantation therapies.

The present invention further relates to a medium for stem cell maintenance, wherein said medium contains, in addition to the nutrients, supplements and growth factors required for cultivation of stem cells, one or more inhibitors of a TRIM-NHL protein. Said inhibitor is preferably a small molecule inhibitor identified and/or optimized in an assay method of the invention as described below.

Suitable media for stem cell maintenance are known in the art and commercially available; examples are media containing Dulbecco's phosphate buffered saline, $MgCl_2$, $CaCl_2$, L-glutamine, non-essential amino acids, antibiotics like penicillin/streptomycin (P/S), Fetal bovine serum (FBS), LIF (Leukemia Inhibitory Factor), 25% (w/v) trypsin-EDTA. Additional factors contained in the medium may be human transferrin, putrescine dihydrochloride, human recombinant insulin, L-thyroxine, tri-iodo-thyronine, progesterone, sodium selenite, heparin, and corticosterone.

Another well described medium for maintenance of neural stem cells is the NS-A medium (Euroclone, Milan, Italy) supplemented with modified N2 (Invitrogen; N2 is a serum-free synthetic medium supplemented with insulin, human transferrin, sodium selenite, putrescine and progesterone) and 10 ng/ml of both EGF and FGF-2 (Invitrogene; Conti et al., 2005).

Yet another maintenance medium for pluripotent stem cells, described in US 20070218548, contains a minimal medium for culturing cells, supplemented with serum, LIF, L-glutamine, 2-mercaptoethanol, and the like; an example of a suitable composition being 85% KnockOut D-MEM (Invitrogen), 15% FBS, $10^{-4}$ M 2-ME, 2 mM L-glutamine, 0.1 mM NEAA (non-essential amino acids, and 1000 U/ml LIF.

Preferably, the medium is a serum-free medium that contains only defined components and supplements.

A medium for neural stem cell maintenance usually contains supplements like N2, bFGF-2 and EGF.

Alternatively to having a TRIM32 inhibitor in the medium, expression of TRIM32 in the cell can be inhibited. The strategies interfering with TRIM32 function administer synthetic oligonucleotides capable of hybridizing with TRIM32 DNA or RNA by one or more nucleotide molecules selected from antisense molecules, ribozymes or small inhibitory RNA molecules (small interfering RNA (siRNA); in the meaning of the present invention, regulatory RNAs such as "micro RNA" ("miRNA") and "short hairpin RNA" ("shRNA") are used interchangeably with the term "siRNA"). In the following, the above-listed TRIM-NHL inhibitors are also referred to as "nucleotide-type TRIM-NHL inhibitors".

A specific embodiment of nucleotide-type TRIM-NHL inhibitors employs the application of RNA interference (RNAi). RNAi is the process of sequence-specific post-transcriptional gene silencing initiated by double-stranded RNA that is homologous in sequence to the silenced gene. Small interfering RNA (siRNA) duplexes of 21 to 22 nucleotides are shown to be a new powerful tool for inhibiting gene function in mammalian cells (Elbashir et al., 2001). Sui et al. (2002) and Brummelkamp et al. (2002a, 2002b) have recently reported vector-based systems for stable expression of short interfering RNAs. These systems are based on a vector, in which a synthetic, gene-specific target sequence encoding the siRNA is expressed under the control of a promoter that is suitable for transcription of small, non-coding RNA. The siRNAs are thus produced from the vector following its introduction into mammalian cells by standard transfection (e.g. electroporation, lipofection) or viral infection protocols (e.g. retroviral infection).

In a further embodiment, the present invention relates to TRIM32 siRNA molecules. Based on the RNA sequence of TRIM32, siRNA molecules with the ability to knock down TRIM32 activity can be obtained by chemical synthesis or by hairpin siRNA expression vectors (as described by Yu et al., 2002) or they may be custom-designed, e.g. by means of the commercially available Dicer siRNA Generation Kit (Gene Therapy Systems), which allows generation of a large number of siRNAs from full-length target sequences. The Dicer siRNA Generation Kit mimics the natural RNA interference process by using recombinant human dicer enzyme, to cleave in vitro transcribed dsRNA templates into a pool of 22 by siRNAs. There are numerous other companies that provide the supply of costum-designed siRNAs on a given RNA sequence, e.g. Ambion, Imgenex, Dharmacon. Methods for selecting designing siRNAs, including selection of the targeted sequence, preparation of the siRNA duplexes, vector design and delivery are well known in the art, e.g. described in detail in U.S. Pat. No. 7,235,654.

The TRIM32 siRNAs of the invention may be chemically modified, e.g. as described in US 2003/0143732, by phosphorothioate internucleotide linkages, 2'-O-methyl ribonucleotides, 2'-deoxy-2'-fluoro ribonucleotides, "universal base" nucleotides, 5-C-methyl nucleotides, and inverted deoxyabasic residue incorporation.

As an alternative to siRNA, antisense oligonucleotides can be used as nucleotide-type TRIM-NHL inhibitors to interfere with the expression of the TRIM32 protein (or another TRIM-NHL protein, respectively).

Thus, in a further embodiment, the present invention relates to antisense molecules directed against a TRIM-NHL protein.

Antisense oligonucleotides are short stretches of nucleotides that are complementary to a region of the target mRNA and can specifically suppress expression of that particular transcript. Examples of antisense oligonucleotides and their use in experimental and clinical settings have been reviewed (Braasch and Corey, 2002; Agrawal et al., 1998; Galderisi et al., 1999; Gewirtz, 1998). The antisense nucleic acid can take the form of RNA expressed from a vector, which has been transfected into the cell or take the form of a DNA or RNA oligonucleotide which can be introduced into cells through a variety of means, e.g. by means of cationic liposomes, cationic porphyrins, fusogenic peptides, and artificial virosomes, or cell permeabilization with streptolysin-O and electroporation. Cationic lipids form stable complexes with oligonucleotides, which exhibit improved cellular uptake (Bennett et al., 1992; Lappalainen et al., 1994), thus resulting in enhanced antisense activity.

Alternatively, TRIM32 can be inactivated by means of ribozymes nucleotide-type TRIM-NHL inhibitors.

In a further embodiment, the invention relates to ribozymes directed against a TRIM-NHL protein. Similarly to antisense oligonucleotides, ribozymes bind to substrate RNA through Watson-Crick base pairing, which leads to sequence-specific cleavage of transcripts. Two types of ribozymes, the hammerhead ribozyme and the hairpin ribozyme, have been extensively studied due to their small size and rapid kinetics. Their application has been reviewed in several publications (Hampel, 1998; Vaish et al., 1998; Birikh et al., 1997; Earnshaw and Gait, 1997; Kore and Eckstein, 1999).

Ribozymes can be imported into the cell by various means, as described above for antisense oligonucleotides, or they can be expressed from a vector, which offers the advantage of continued intracellular production of these molecules (Irie et al., 1999; Smith et al., 1997).

Preferably, the nucleotide-type TRIM-NHL inhibitors are produced from a viral vector, e.g. a retroviral or adenoviral vector, an adeno-associated viral vector or lentiviral vector.

Based on the gene function-inhibitory methods described above and the published sequence of the human TRIM-NHL genes, the person skilled in the art can determine the TRIM-NHL siRNA, antisense or ribozyme target sequences and construct vectors for transfection or infection of stem cells, e.g. a TRIM32 RNAi construct containing the sequence GATCTTCAGGCAAGGTATA (SEQ ID NO:7).

Stem cells and progenitor cells with reduced or absent expression of a TRIM-NHL protein due to the action of one or more nucleotide-type inhibitors as described above are useful for transplantation therapies.

Alternatively to the above-described nucleotide-type molecules, small molecule compounds can be used to modulate TRIM32 activity in vitro or in vivo. The present invention provides methods for identifying and/or characterizing such compounds. The methods of the invention are based on findings of the invention that the differentiation regulatory effect of TRIM32 can be mediated by two binding-partners of TRIM32, namely the proto-oncogene Myc and the miRNA-associated protein Argonaute-1 (Ago-1).

Thus, the present invention relates to a method for determining whether a test compound has the ability to modulate the proliferation and/or differentiation potential of stem cells, wherein said test compound is tested for its ability to modulate the activity of a TRIM-NHL protein selected from TRIM32 (SEQ ID NO:2), TRIM2 (SEQ ID NO:4) or TRIM3 (SEQ ID NO:6), said activity being selected from a) transfer of ubiquitin by said TRIM-NHL protein from a ubiquitin conjugating enzyme E2 to Myc or
b) binding of said TRIM-NHL protein to Argonaute-1,
wherein a change in the level of activity of said TRIM-NHL protein in the presence of the test compound, as compared to the level of TRIM-NHL activity in the absence of the test compound, is indicative of the compound's ability to modulate the proliferation and/or differentiation potential of stem cells.

The activity defined in a), i.e. binding of the TRIM-NHL protein (e.g. TRIM32) to Myc and ubiquitination of Myc, results in degradation of Myc via the ubiquitin-proteasome system.

The activity defined in a), i.e. binding of the TRIM-NHL protein (e.g. TRIM32) to Myc and ubiquitination of Myc, results in degradation of Myc via the ubiquitin-proteasome system.

In the assay method of the invention according to variant a), in a preferred embodiment, the TRIM-NHL protein, e.g. TRIM32, is incubated, together with Myc, a ubiquitin activating enzyme (E1), a ubiquitin conjugating enzyme (E2), ubiquitin and ATP for a period of time sufficient to obtain a measurable level of ubiquitin associated with Myc, and the level of ubiquitination of Myc in the presence or absence of a test compound is compared, and wherein a change in the level of Myc ubiquitination in the presence of the test compound, as compared to the level of Myc ubiquitination in the absence of the test compound, is indicative of the compound's ability to modulate the proliferation and/or differentiation potential of stem cells. If the compound is an inhibitor of TRIM32, it is a candidate stem cell maintenance agent.

For the present invention, the term "Myc" encompasses c-Myc or any of its relatives that are susceptible to the ubiquitination reaction mediated by TRIM32, i.e. n-Myc or 1-Myc.

The components for the assay can be obtained as follows:

The proteins used in the screening assay are preferably recombinant proteins, which can be obtained according to conventional methods by transforming a suitable host with a plasmid carrying the sequence encoding the protein. The cDNA sequences encoding the protein components TRIM-NHL protein (TRIM32: SEQ ID NO:1; TRIM2: SEQ ID NO:3; TRIM3: SEQ ID NO:5), E1, E2, Myc and ubiquitin are available from the literature and from databases.

The assay components TRIM-NHL protein (e.g. TRIM32 (SEQ ID NO:2; GenBank Accession Nos. NM_012210 and NM_053084), or a fragment thereof that contains the RING finger domain E2 and ubiquitin, are usually produced and purified as fusion proteins. The proteins may be fused to an affinity tag, which is a protein suitable for affinity purification, such as gluthathion S-transferase (GST, Amersham Pharmacia), maltose binding protein (MBP, New England Biolabs), chitin binding domain (New England Biolabs), the myc-epitope (EQKLISEEDL) or the His(6) tag (Qiagen, Novagene). The fusion protein can be expressed, e.g. in *E. coli*, and purified according to standard protocols.

The substrate protein Myc and DNA sequences encoding it are known from the literature and from data bases, e.g. c-Myc (GenBank Accession No. P01106), 1-myc (GenBank Accession No. AA038672) or n-myc (GenBank Accession No. P04198). Instead of using the full-length protein, a fragment that contains the relevant site for ubiquitination by TRIM32 can be used. A suitable fragment and its size can be easily determined in preliminary experiments by employing different sized TRIM32 peptide fragments in the desired assay format and determining suitable peptides that are amenable to the ubiquitination reaction.

E1 may be purified due to its reversible interaction with ubiquitin according to known methods (e.g. Hatfield et al., 1990; Hatfield and Vierstra, 1992); E1 is also commercially available (e.g. Boston Biochem). In the case of using untagged ubiquitin, a commercially available product (e.g. from Sigma, Fluka) may be used as this assay component.

Preferably, the naturally occurring proteins are used; however, the proteins may contain deviations from the natural amino acid sequence as long as these deviations do not impair their functional activity.

A suitable ubiquitin activating enzyme (E1) is the wheat UBA1 E1 (GenBank Accession No. M55604), however, UBA1 E1 from other species, e.g. from *Xenopus laevis*, may also be used. E1 can be purified on a ubiquitin affinity matrix according to published procedures (e.g. Hatfield et al., 1990; Hatfield and Vierstra, 1992).

As ubiquitin conjugating enzyme (E2), in a preferred embodiment, the human variant UBCH5b (GenBank Accession No. U39317) is used, although, also in this case, UBCH5b homologues from other species, e.g. *Xenopus laevis*, may be employed. Alternatively, UBCH5a (GenBank Accession No. AAH05980) or UBCH5c (GenBank Accession No. AAH66917) can be used. Alternatively, ubiquitin conjugating enzymes different from UBCH5a, b or c can be used, as long as these enzymes support the transfer of ubiquitin to Myc. Preferably, the ubiquitin conjugating enzyme E2 is fused to an affinity tag which is selected from the ones listed above as suitable for TRIM32, but different from the tag chosen for TRIM32. For example, in the case that GST-TRIM32 is used, His(6) or another tag different from GST is used for tagging E2.

To sustain a sufficient ATP level during the entire ubiquitination reaction, a so-called "ATP regenerating system" (e.g. comprising 0.5 mM ATP, 60 μg/ml creatine phosphokinase, 6.6 mM phosphocreatine, 10 mM Tris-HCl, 0.5 mM $MgCl_2$, 1 mM KCl, 0.05 mM DTT) may be advantageously employed (Murray, 1991).

Ubiquitin is commercially available (Sigma), it may also be recombinantly produced; in this case it may be fused to various tags for purification, i.e. His(6), GST or for detection, i.e. myc-epitope, HA-epitope. In both cases, ubiquitin comprises the N-terminal 76 amino acids required for its function. Preferably, a tagged ubiquitin is employed in the assay. The ubiquitin used in the assay may also carry a non-proteinacious tag, e.g. biotin.

The above-described assay essentially comprises the steps of the ubiquitination reaction itself and the step of measuring the extent of ubiquitin transfer to Myc. The first step comprises reacting the assay compounds listed above for a period of time sufficient to allow for the ubiquitination reaction, e.g. for 30 min.

The reaction may either be conducted in solution by simply mixing the assay components, or alternatively, the reaction may be carried out by using immobilized Myc. In this case, Myc carries an affinity tag (GST or one of the alternative tags mentioned above) that is used for its binding to a solid phase carrying the ligand for the respective affinity moiety, e.g. glutathione agarose or sepharose beads or microtiter plates coated with antibodies against the affinity moiety, e.g. commercially available anti-GST antibodies.

After the reaction has been completed, the amount of ubiquitin associated with Myc can be measured in different ways: In case the ubiquitination reaction has been carried out in solution, the affinity-tagged, e.g. GST-tagged, Myc is captured on microtiter plates that are coated with an antibody against GST (this step can be omitted in case the reaction has been carried out with TRIM32 bound to a solid phase). The unbound GST-MYc, the unincorporated ubiquitin and the other reaction partners are then washed off. Subsequently, the immobilized ubiquitin can be visualized by using an antibody that is directed against a tag epitope, e.g. the myc-epitope present in the recombinant tagged ubiquitin, which antibody carries a detectable label. Suitable labels are radioactive labels, e.g. $^{125}I$, enzymatic labels, e.g. horseradish peroxidase or alkaline phosphatase, or fluorometric labels. In a preferred embodiment, quenched fluorophors, e.g. Europium (Wallac/PerkinElmer) that will be dequenched upon incubation with an enhancer solution (Wallac/PerkinElmer), are used. The obtained values are compared to values obtained from reactions without Myc (negative control, background) and to values obtained from a reaction mixture incubated in the presence of the solvent (usually DMSO) only (positive control).

Alternatively to using the ELISA type assay described above to detect the amount of bound ubiquitin, the physical proximity of ubiquitin molecules associated with Myc upon incubation at 37° C. can be utilized to measure the extent of ubiquitin association with Myc by fluorescence resonance energy transfer (FRET, as described by Gershkovich et al., 1996, or by Matayoshi et al., 1990, He et al., 2003, or reviewed by Selvin, 2000). FRET can only be achieved if certain conditions are fulfilled, i.e. fluorophor pairs with overlapping emission and excitation wavelengths, like europium/allophycocyanin, europium/Cy5, europium/PE (all commercially available from Wallac/PerkinElmer) and an minimal proximity of these fluorophors below 5-10 nM. These fluorophors can be added either bound to antibodies directed against the affinity label, e.g. GST, or the epitope, e.g. the myc epitope, or can be directly coupled to Myc or ubiquitin (custom service of Wallac). When coupled to antibodies, the fluorophors are added to the reaction after its completion. No further washing steps are necessary and signals (excitation at 340 nm and emission measurement at 665 nm in the case of the FRET pair allophycocyanin and europium) are measured after incubation at 4° C. for 30 min, allowing the binding of the antibodies and the subsequent energy transfer between the fluorophors. In case of direct labeling of reaction components, i.e. ubiquitin or Myc, real time measurements can be performed allowing the detection of kinetic differences in the reaction.

In a further aspect, the method of the invention is conducted in the high throughput format. By way of example, such an assay is performed in 96 or 384 well plates in a suitable reaction volume, e.g. 50 μl, in the absence or presence of the test compounds, which are usually dissolved in DMSO.

In the case of a screening assay, compounds identified as positive are next confirmed to be specific inhibitors of TRIM32 activity and not to be inhibitors of the other enzymes present in the reaction mixture. Such secondary assays can be conducted as described in WO 2005/113789.

The assay variant b) as defined above is based on the interaction of the TRIM32 protein with Argonaute-1.

In this embodiment, TRIM32 or a fragment thereof containing or consisting of the domain of TRIM32 that interacts with Argonaute-1, i.e. the NHL domain, is immobilized on a solid support, either directly or through a tag. (Suitable tags are commercially available, e.g. the FLAG, HA, MYC, HIS, MBP tag, etc.). Examples for solid supports are commercially available immunobeads, immunoplates or microchips, carrying the ligand for the respective affinity moiety, e.g. glutathione agarose, or sepharose beads, or microtiter plates coated with antibodies against the affinity moiety, e.g. commercially available anti-GST antibodies etc.

The Argononaute-1 protein, preferably human Ago-1 (GenBank Accession No. Q9UL18) or a fragment thereof that contains or consists of the domain that interacts with TRIM32 is modified with a suitable label to allow for rapid detection (i.e. radio-labeled, fluorescently labeled, hapten-labeled etc.) and incubated in the presence or absence of the test compounds. Examples for suitable labels are commercially available radioactive or fluorescence labels like europium or other lanthanides, hapten labels, peptide labels, or the Green Fluorescent Protein (GFP), an enzyme label, e.g. luciferase, alkaline phosphatase etc.).

After an incubation period that allows for interaction of the proteins, e.g. for about 20 minutes at 25° C., the amount of Argononaute-1 bound to the immobilized TRIM32 is measured by use of the label outlined above or by the use of suitable antibodies in an ELISA type assay. The assay may also be set up in the reverse, e.g. with TRIM32 being labeled and with Argononaute-1 immobilized, or by performing the binding reaction in solution and then capturing one of the components on a solid support and measuring the amount of the other component that is co-immobilized. An example of a commercially available assay of this type is the Delfia Assay (Wallac/PerkinElmer) that uses Europium or another lanthanide as a label.

The assay variant b), based on the interaction between TRIM32 and Argonaute-1 may also be in the format of a FRET assay, as described above, which measures protein interactions at the molecular level by fluorescence resonance energy transfer using a pair of fluorescent proteins, such as CFP and YFP, in which the emission spectrum of CFP significantly overlaps the excitation spectrum of YFP. The resulting energy emitted from the donor CFP protein can directly excite the acceptor YFP protein when the proteins are closely approximated. During FRET, there is quenching of the emission of the donor CFP protein that is directly related to the efficiency of energy transfer and inversely proportional to the sixth power of the distance between the donor and acceptor proteins.

Alternatively to using CFP and YFP, a pair of synthetic fluorophores can be used, which are commercially available, e.g. allophycocyanin and europium (Wallac/PerkinElmer). In brief, each of the recombinantly produced binding partners can be labeled, depending on the fluorophore either directly or, in the case of allophycocyanin usually indirectly, with one of the fluorophores. To facilitate coupling of the fluorophores, tagged interaction partners (GST, Myc, His, MBT) and anti-tag antibodies carrying the fluorophore may be used. Such assays are commercially available, e.g. LANCE ULTRA (PerkinElmer). The assays based on FRET are usually done in vitro, but may also be done in living cells, as described by He et al., 2003.

A similar type of assay employs the Alpha Screen technology (PerkinElmer), which is based on the use of donor and acceptor beads. A signal depends, as in the FRET assay, on the physical proximity of the binding partners, each of which carries a tag that the beads can bind to. This assay technology has the advantage that reliable signals are generated even when the interaction partners are not in close proximity.

Another assay system for determining a compound's effect on the TRIM32/Argonaute-1 interaction is based on fluorescence correlation spectroscopy (FCS; Magde et al., 1974; Rigler et al., 1993; Maiti et al., 1997), which is a high-resolution spatial and temporal analysis that measures, even in low concentrations, fluctuations of the fluorescence signals from one of the binding partner that is fluorescence-labeled. In contrast to other fluorescence techniques, the parameter of primary interest is not the emission intensity itself, but rather spontaneous intensity fluctuations. FCS is a well established method, it has also been used in high-throughput screening (Eigen and Rigler, 1994; Auer et al., 1998; Rogers, 1997). Another suitable method of the invention applies dual-colour fluorescence cross-correlation spectroscopy (dual-colour FCS; Schwille et al., 1997; Kettling et al., 1998), a further development of FCS. Because it combines two different fluorophores, dual-color FCS improves on conventional FCS in terms of analysis speed, specificity, and sensitivity.

In yet another embodiment, the assay method is fluorescence cross-correlation spectroscopy (FCCS), which is a derivative of the FCS technique, detecting the synchronous movement of two biomolecules with different fluorescence labels. This method can be conducted both in vitro and in living cells, as described, for example, by Thews et al., 2005.

Both for FCS and FCCS, specialized detection instruments are commercially available, e.g. (Evotec Clarina II).

In another embodiment, the assay to detect a compound's effect on the interaction between TRIM32 and Argonaute-1 is a Biacore assay. Biacore biosensors are widely used; they are based on a label-free technique called "surface plasmon resonance" to detect changes in refractive index that occur when two molecules bind together, resulting in an increase in mass at the detecting surface, whereby binding and dissociation events are measured in real-time.

Apart from the Biacore methodology, other recent commercially available label-free optical biosensor technologies (reviewed by Cooper, 2006) are suitable as assay formats in the method of the invention, e.g. methods that detect changes in local index of refraction and allow for assaying the effect of compounds on the interaction of unlabeled binding partners in the HTS format by immobilizing one of the binding partners on specialized microtiter plates, applying the second partner and measuring the emitted signal. Such a system is commercially available as Corning® Epic™ system: Resonant waveguide grating (RWG) sensors are chemically modified with a surface layer that enables covalent attachment of protein targets. The surface chemistry provides a high-binding-capacity surface, with low levels of non-specific binding. After one of the binding partners is immobilized, the reader obtains a baseline measurement. Subsequently, when the other protein binds to its immobilized partner, a change in the local refractive index is induced, which results in a shift in the wavelength of light that is reflected from the sensor. The magnitude of this wavelength shift is proportional to the amount of protein bound to the immobilized binding partner.

Another commercially available label-free system for measuring the effect of a test compound on the interaction of TRIM32 with Argonaute-1 is the SRU BIND™ system, which is comprised of microplates with specialized detection instruments. Photonic crystal optical biosensors are incorporated into the bottom surface of the microplate wells, and are designed to reflect only a very narrow band of wavelengths when illuminated with a broad band of incident wavelengths. The photonic crystal tightly confines resonantly coupled light to the device surface, resulting in a shift of the reflected wavelength ("Peak Wavelength Value" or "PWV"), when biomolecules bind to the biosensor surface.

Another suitable label-free method uses the so-called Octet system (ForteBio), based on "BioLayer Interferometry" (BLI). This system uses disposable sensors with an optical coating layer at the tip of each sensor. This optical surface is coated with a biocompatible matrix that can interact with molecules from a surrounding solution. The instrument then shines white light down the biosensor and collects the light reflected back. Interference patterns in the reflected light are captured by a spectrometer as a characteristic profile of wavelength peaks and troughs. When biomolecules bind to the biosensor surface, its thickness increases and the binding can be monitored by analyzing changes in the interference pattern at the spectrometer.

The above-described assays are mostly amenable to the HTS format and may therefore be used for screening modulators of the TRIM32/Argonaute-1 interaction.

In another embodiment, the assay of the invention may be based on the effect that binding of TRIM32 to Argonaute-1 can change the specificity and/or activity of Argonaute-1 towards certain micro-RNA's. It is found that the expression of TRIM32 in neural stem cells affects the levels of the micro-RNA's 146b, 489, 615, 26a, 129-3p, 34a and 92. Hence, such changes can be a readout for inhibition of the TRIM32-Ago1 interaction measuring miRNA levels via quantitative PCR, Northern-Blot or micro-arrays.

Furthermore the inventors could demonstrate that TRIM32 is physically associated with a certain set of miRNA's. This finding can also be utilized for an assay to determine a compound's effect on TRIM32 by immunoprecipitating TRIM32 in the presence and absence of test compounds and subsequently determining the amount of associated mRNAS on microarrays. (miRNAs are about 22-nucleotide long, non-coding RNAs that are thought to regulate gene expression through sequence-specific base pairing with target mRNAs. Up to now hundreds of miRNAs have been identified in worms, flies and mammals. MircoRNAs are transcribed as long RNA precursors (pri-miRNAs) that contain a stem-loop structure of about 80 bases. Pri-miRNAs are processed in the nucleus by the Rnase III enzyme Drosha and DGCR8/Pasha, which excises the stem-loop to form the pre-miRNA. Then pre-miRNAs are exported from the nucleus via Exportin-5. In the cytoplasm the RNase III Dicer cuts the pre-miRNA to generate the mature miRNA as part of a short RNA duplex. This RNA is subsequently unwound and incorporated in the RNA-induced silencing complex (RISC). This RISC complex contain Argonaute family proteins. MicroRNAs in animals are thought to function either through the inhibition of effective mRNA translation of target genes through imperfect base pairing with the 3'-untranslated region of the target mRNA or through perfect base pairing mediated degradation of the target mRNA. MicroRNA targets are largely unknown, but estimations range from one to hundreds of targets for a given miRNA.)

In spite of the promising therapeutic potential of stem cell transplantation therapies, in particular using neural stem (NS) cells, in various disease conditions, there are general concerns relating to potential immune rejections after transplantation and because of ethical issues regarding the use of human embryos to obtain ES cells. Although the latter concerns are less serious for adult stem cells, there is a need for drugs that can directly act on the adult stem cells in the body to maintain and/or increase their proliferation potency in the relevant tissue.

Therefore, in one embodiment, a method is provided for modulating the proliferation and/or differentiation potential of progenitor cells and stem cells in a subject, including administering a therapeutically effective amount of an agent that modulates the level of expression and/or activity of a protein from the TRIM-NHL protein family in said cells, and a pharmaceutically acceptable carrier.

The present invention also relates for pharmaceutical compositions useful in such methods.

In view of promoting proliferation of the stem cells, the agent is an inhibitor of a TRIM-NHL protein.

In certain embodiments, the protein of the TRIM-NHL family is selected from TRIM2, TRIM3 and particularly, TRIM32.

The therapeutically active agent may be any pharmaceutically acceptable agent that has been described above for the in vitro use of TRIM32 modulators. Hence, in certain aspects, the TRIM32 modulator is a nucleotide-type molecule that prevents or decreases TRIM32 expression in the cells, e.g. an antisense, ribozyme or siRNA molecule, as described above for in vitro inhibition.

For delivery of the nucleotide-type inhibitor, methods are well known in the art.

In one embodiment, the constructs encoding the nucleotide-type TRIM-NHL inhibitors are delivered to cells by transfection, i.e. by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, dendrimers and liposomes. A colloidal system may be a lipid-complexed or liposome-formulated nucleotide-type inhibitor. Formulation of the inhibitor, e.g. with various lipid or liposome materials, may then be effected using known methods and materials and delivered to the recipient cell or mammal.

In a preferred method of the invention, the nucleic acid molecules are delivered by viral vectors. The nucleic acids may be incorporated into any of a variety of viral vectors useful in gene therapy, such as recombinant retroviruses, adenoviruses, adeno-associated viruses (AAV), or herpes simplex virus-1.

For the purpose of viral delivery, lentiviral vectors have been considered particularly useful, as they have been shown to successfully infect primary cells (Luther-Wyrsch et al., 2001). Furthermore, lentiviral vectors have already proven to be suitable for in vivo gene therapy applications due to the following characteristics (Buchschacher et al., 2000; Vanden-Driessche et al., 2002): Since lentiviruses (a genus of the retrovirus family) are stably integrated into chromosomal DNA and have little tendency to be epigenetically silenced, they offer the potential for long-term expression. Moreover, lentiviral vectors can efficiently transduce dividing as well as non-dividing cells.

To achieve TRIM32 inhibition, expression cassettes encoding TRIM32-inhibiting oligonucleotide molecules are inserted into lentiviral vectors (Lever, 1996; Follenzi et al., 2002). These vectors are then transfected by standard methods (e.g. electroporation, lipofection) into specialized packaging cells (Kafri et al., 1999) to generate pseudotyped lentiviruses for infection of human stem cells.

The nucleotide-type TRIM-NHL inhibitor, e.g. an siRNA or nucleic acid encoding it, is preferably administered locally in the tissue of interest—i.e. the subventricular zone, for example, a therapeutically effective amount of a TRIM32 siRNA or nucleic acid encoding it can be administered into the brain of a patient.

Another method for delivering the nucleotide-type inhibitors is by means of DNA nanoparticles encapsulated in 3D tissue-engineered scaffolds that have been recently described to enhance osteogenic differentiation of mesenchymal stem cells (Hosseinkhani et al., 2007).

To target the nucleotide-type inhibitors to the adult stem cells of interest, tissue specific promotors in the vector constructs can be used. These specific promotors ensure that the nucleotide-type inhibitors are only produced in the stem cell of interest. Examples for such promotors are the Nestin promotor or the Sox2 promotor for neural stem cells, the Pax7 promotor for muscle stem cells and the Pax3 promotor for skin stem cells.

To determine whether and at which concentration a candidate TRIM-NHL modulator, e.g. an inhibitor (designed as a nucleotide-type inhibitor or a small molecule identified and/or optimized in an assay method of the invention) is effective, e.g. for maintenance of neural stem cell pools, neural stem cells are transferred into culture as described by Conti et al., 2005. To test the candidate compound, neuronal differentiation is induced by suitable cell culture conditions. This process will be blocked upon addition of an efficient TRIM-NHL inhibitor. By using various concentrations of the candidate compound, the minimal concentration that is able to inhibit neuronal differentiation can be determined.

In contrast, an efficient activator would induce neuronal differentiation, even under conditions where the cells usually keep their stem cell status (i.e. is under growth conditions with EGF and FGF-2). Neuronal differentiation or stem cell maintenance can be visualized by immuno fluorescence stainings with antibodies against Nestin (stem cell marker) and TuJ1 (neuronal marker).

Activators of TRIM-NHL are useful in the therapy in diseases where excessive proliferation of undifferentiated tissue is proven or speculated to be involved. This includes—but is not limited to—lung fibrosis and all other types of fibrotic diseases.

The concentrations that have been determined in this tissue culture assay can be used as a starting point for animal experiments and clinical trials.

In vivo activity of TRIM-NHL modulators on neuronal stem cell proliferation and migration through the rostral migratory system can be tested in analogy to the experiments with dopamine receptor agonist as described by Höglinger et al., 2004; Winner et al, 2006. Other models may involve the Huntington's disease mouse model like the R6/1 or R6/2 model (reviewed by Li et al., 2005) or seizure models (e.g. as described by Morgan et al., 2006).

The pharmaceutical compositions containing a TRIM-NHL modulator, in particular an inhibitor, are preferably prepared and administered in dose units. For treatment of a subject, e.g. but not limited to a human subject, and depending on the activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administrations of subdivided doses at specific intervals.

The pharmaceutical compositions can be administered systemically or locally, such as, but not limited to, by direct injection into the tissue of interest. The compositions are in general administered intravenously, intramuscularly, as implants, or topically, e.g. for skin lesions.

Suitable pharmaceutical preparation forms are, for example, injectable solutions in ampule form, emulsions, suspensions, creams, aerosols, preparations with sustained release of active compounds.

The TRIM-NHL modulators and pharmaceutical compositions containing them are useful for in vitro and in vivo application on various types of stem cells. Examples are, without limitation: hematopoietic stem cells giving rise to blood cells; bone marrow stromal cells (mesenchymal stem cells) that give rise to e.g. bone cells (osteocytes) and cartilage cells (chondrocytes); multipotent peripheral blood stem cells (PBSCs); adult bone marrow stem cells with the potential to give rise to hepatocytes, cardiomyocytes, neural cells and muscle cells; neural stem cells in the brain giving rise to nerve cells (neurons) as well as non-neuronal cells (astrocytes and oligodendrocytes); epithelial stem cells giving rise to e.g. absorptive cells, goblet cells, Paneth cells, and enteroendocrine cells; skin stem cells (epidermal stem cells giving rise to keratinocytes and follicular stem cells giving rise to the hair follicle); umbilical cord blood stem cells; hepatic stem cells giving rise to pancreatic endocrine hormone-producing cells; pancreatic stem and progenitor cells, giving rise to islet cells; stem cells and progenitor cells of the eye (corneal and retinal stem cells); mesoangioblasts (vessel-associated stem cells).

By way of example, bone marrow cells and cord blood stem cells are therapeutically useful for blood disorders such as leukemia, multiple myeloma and lymphoma.

Stem cells from bone marrow and peripheral blood may be injected either into the coronary arteries or directly into the myocardium for treating severe ischaemic heart disease, transplantable cells including mesenchymal stem cells from bone marrow and CD34+ cells from peripheral blood. Therapeutic benefit may be increased vascularization of myocardium, and formation of new myocardial cells.

Application of a TRIM-NHL inhibitor on neural stem cells may be beneficial for the therapy of neurodegenerative disorders like Parkinson disease, Alzheimer's disease, schizophrenia, Huntington disease, for the regeneration of the nervous system after injuries as well as for the treatment of muscular dystrophy and wound healing. For most of these diseases, the drug is applied by direct injection at the site of the lesion. However, also an application into the bloodstream, or as an ointment (e.g. for skin healing) is possible. The dosage of the drug should be in the nanomolar to picomolar range.

Application to pancreatic stem or progenitor cells has potential for the treatment of type I diabetes. Application on eye stem cells has been suggested for corneal and retinal degenerative disease, e.g. macula degeneration. Mesoangioblast stem cells hold, after successful experiments with dogs, great promise for the treatment of muscular dystrophy, skin stem cells (epidermal and follicular stem cells) for wound healing and hair loss.

In a further aspect, the invention relates to the use of
a) a DNA molecule of SEQ ID NO: 1, SEQ ID NO:3 or SEQ ID NO:5 or a variant encoding a polypeptide with at least about 80% identity with a TRIM-NHL protein of SEQ ID NO:2, SEQ ID NO:4 or SEQ ID NO:6, or a fragment thereof or a complement thereto, or of
b) a TRIM-NHL protein of SEQ ID NO:2, SEQ ID NO:4 or SEQ ID NO:6, or a variant with at least about 80% identity or a fragment thereof, for the generation of an modulator of the biological function of a TRIM-NHL protein.

In particular, this use relates to the generation of TRIM-NHL protein inhibitors that are useful for stem cell maintenance.

While the invention has been primarily conceived and developed for application on human stem cells and progenitor cells, it is also useful for application on animal cells. Upon having determined that a modulator of a human TRIM-NHL protein, e.g. a small molecule TRIM32 inhibitor, is also effective on animal cells, e.g. mouse stem cells, such modulator can e.g. be incorporated into a culture medium for maintenance of mouse stem cells. Alternatively, a nucleotide inhibitor directed against the respective mouse TRIM-NHL protein homologue may be designed.

BRIEF DESCRIPTION OF THE FIGURES

FIG. 1: Comparing the distribution of TRIM32 during asymmetric and symmetric cell division FIG. 2: Induction of neuronal differentiation by TRIM32 and inhibition of differentiation by TRIM32 RNAi

FIG. 4: Binding of TRIM32 to Argonaute 1 and effect on microRNAs

MATERIALS AND METHODS

Figure 3:
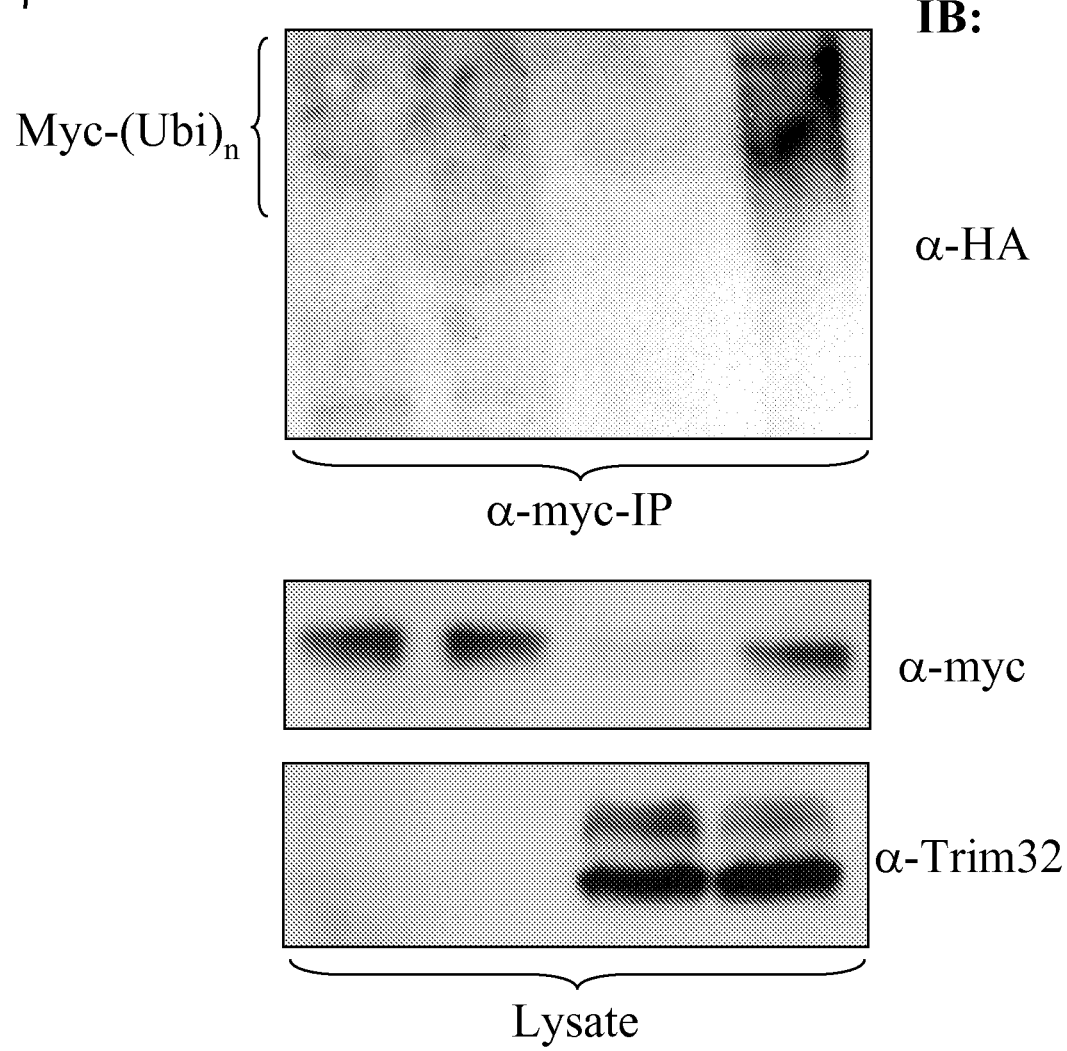
FIG. 3: Myc ubiquitination by TRIM32

If not otherwise stated, in the Examples, the following Materials and Methods are used:
i) Histochemistry Immunohistochemistry on 10 μm cryosections of paraformaldehyde-fixed embryos is performed as described by Calegari et al., 2002.

Embryos are fixed overnight at 4° C. in 4% paraformaldehyde in 120 mM phosphate buffer, pH 7.4, equilibrated in 30% sucrose in PBS and embedded in Tissue-Tek. Cryosections (10 μm) are prepared, permeabilized with 0.3% Triton X-100 in PBS, quenched with 10 mM $NH_4Cl$, and subjected to immunohistochemistry according to standard procedures. Images are collected by using LSM software (Zeiss), and fluorescence of defined regions is quantified by using IMAGE J software.
ii) Transfections of Neural Stem Cells Neural stem cells are transfected via in utero electroporation (Shu et al., 2006). After electroporation, the complete brain is disintegrated and the dissociated cells are cultured in NSA medium with 2 mM L-glutamine, 100 U/ml penicillin, 100 μg/ml streptomycin, 10 ng/mL bFGF-2, 10 ng/mL EGF and 1% N2 supplement. The process of electroporation and cultivation has been described previously (Shu et al., 2006). Four days or six days after transfection the cells are fixed with 4% PFA and processed for immunohistochemistry. The following antibodies are used for immunohistochemistry: anti-Nestin antibody (BD Biosciences) anti-TuJ1 antibody (Covance).

The following plasmids are used: EGFP-N1 (Clontech), EGFP-TRIM32 (pcDNA3.1 vector, Invitrogen) and TRIM32-RNAi (pSM2 vector, Open Biosystems).
iii) Cell Culture HEK293T cells are grown in DMEM supplemented with 10% heat-inactivated FCS, 2 mM L-glutamine, 100 U/ml penicillin and 100 μg/ml streptomycin. They are transfected with Fugene (Roche) according to the instructions of the manufacturer.

HEK293T cells are lysed 48 h after transfection with lysis buffer 1 (2% Triton X-100 and Complete protease inhibitor cocktail (Roche) in PBS) for 30 min at 4° C. For inhibition of the proteasome, the drug clasto-Lactacystin β-Lactone (β-Lactone, Sigma) is used as indicated. For Western-Blots, the following antibodies are used: anti-Myc antibody (Santa Cruz Biotechnology), anti-HA antibody (Roche), anti-Ago1 antibody (a polyclonal rat antibody), anti-TRIM32 antibody (see Example 1).
iv) miRNA Experiments Neural stem cells are transfected with vectors for EGFP or EGFP-TRIM32 as described above. After four days in culture, transfected cells are collected via fluorescence-activated cell-sorting (FACS). From these cells the total RNA is isolated with the miRNeasy Kit (Quiagen). From these samples differentially regulated miRNAs are determined by LNA (Locked Nucleic Acid) microarrays (Exiqon).

EXAMPLE 1

Asymmetric Distribution of TRIM32

Embryonic mouse brains are collected at embryonic day 12.5 (E12.5), after fixation (16 h with 5% paraformaldehyde) and dehydration (16 h with 20% Succhrose) the brains are sliced in 10 μm thick pieces. Dividing neural stem cells in the ventricular zone of the developing forebrain are stained with Phalloidin-Alexa-555 to stain actin filaments that highlight the outline of the cell with HOECHST to label DNA and with an antibody against TRIM32. The antibody is produced by immunization of rabbits with a TRIM32 peptide stretching (aa 25 to aa 39 of seq, followed by affinity purification of the gained serum.

In order to generate neurons, neural stem cells can divide asymmetrically (with a horizontal cleavage plane). In such a neurogenic cell division, the more apical daughter cell retains the stem cell characteristics, while the more basal daughter cell leaves the cell cycle and becomes a postmitotic neuron. This staining shows that TRIM32 is usually enriched in the basal daughter cell and is therefore asymmetrically segregated in the cell that will become a neuron Neural stem cells can also divide symmetrically (with a horizontal cleavage plane). The two daughter cells of such a symmetric cell division both retain stem cell features. In the diagram (FIG. 1) the distribution of TRIM32 during asymmetric- (apical and basal daughter cell) and symmetric (medial and lateral daughter cell) cell division is compared. It is shown that TRIM32 is distributed equally during symmetric cell division, while it is enriched in the basal daughter cell during asymmetric cell divisions. Therefore it may be assumed that the basal localization of TRIM32 is an instructive signal for the basal daughter cell to differentiate into a neuron.

EXAMPLE 2

Induction of Neuronal Differentiation by TRIM32 and Inhibition of Differentiation by TRIM32 RNAi To investigate how TRIM32 influences the fate of neural stem cells, these cells are transfected with a gain of function construct for TRIM32 (an expression vector for EGFP-tagged TRIM32; E/TRIM32) and a TRIM32 loss of function construct (an expression vector for a short-hairpin RNA that is directed against TRIM32; TRIM32-RNAi). As a control the NSC's are transfected with an EGFP expression plasmid. The question that should be answered with these experiments is whether a TRIM32 gain of function or loss of function affects the differentiation status of the NSC's.

The NSC's are transfected via in utero electroporation followed by a four (FIGS. 2a and b) or six (FIGS. 2c and d) day incubation under defined culture conditions that allow neuronal differentiation (as previously described in Shu et al., 2006). After this incubation, the cells are fixed and the differentiation status of the transfected cells is determined through immuno fluorescence stainings with antibodies against Nestin (an intermediate filament protein that serves as a stem cell marker) or TuJ1 (a tubulin iso form that is specific for neurons, therefore this staining serves as a neuronal marker).

After four days in culture only a minority of cells that express TRIM32 are still stem cells, while nearly 75% of the EGFP or TRIM32-RNAi expressing cells are still stem cells (a). In contrast to this around 50% of the TRIM32 expressing cells differentiated into neurons, while only a minority of the EGFP or TRIM32-RNAi expressing cells shows neuronal characteristics (b). After four days in culture there is no difference in cell fate between cells expressing EGFP or expressing TRIM32-RNAi, therefore it seems that an absence of TRIM32 does not influence the cell fate. But after six days under conditions allowing differentiation, the effect of TRIM32 absence becomes visible. After six days on 25% of the EGFP expressing cells are still stem cells, while more than 50% of the cells that do not express any TRIM32 (TRIM32-RNAi) are still in the stem cell status (c). Furthermore, more than 25% of the EGFP expressing cells differentiated into neurons, while below 10% of the TRIM32-RNAi expressing cells shows neuronal differentiation (d). From this results we conclude that TRIM32 activity promotes neuronal differentiation, while absence of TRIM32 favours preservation of stem cell features.

EXAMPLE 3

Myc Ubiquitination

From the previous experiments it becomes clear that TRIM32 is able to induce neuronal fate in neural stem cells. The next question that needs to be answered is which mechanism is utilized by TRIM32 to accomplish this function. When TRIM32 is overexpressed, the formation of so called aggresomes, that are positive for the transcription factor and oncogen Myc, can be observed (data not shown). Because TRIM32 has a Ring-Finger domain and thereby has the potential to function as an ubiquitin ligase, it is tested if TRIM32 ubiquitinates Myc, and thereby marks it for degradation via the ubiquitin-proteasome system (UPS). In HEK293T cells expression plasmids for HA-Ubiquitin, EGFP, TRIM32 and Myc are coexpressed as indicated in FIG. 3. If Myc is ubiquitinated by TRIM32 inhibition of the UPS should lead to an accumulation of high molecular weight forms of Myc (Myc-(Ubiquitin)$_n$). Therefore the UPS in the transfected cells is inhibited by treatment with clasto-Lactacystein β-Lactone (β-Lactone) as indicated in FIG. 3. After precipitation of Myc with an anti-Myc antibody, Myc-associated ubiquitin is detected with an anti-HA antibody (upper penal). In the absence of TRIM32 only a low amount of poly-ubiquinated Myc can be detected (lanes 1 and 2). In contrast to this, when TRIM32 is expressed and the UPS is not inhibited, no poly-ubiquitin-Myc can be detected, this is because TRIM32-catalyzed ubiquitination leads to degradation of Myc, as long as the UPS is active (see reduced Myc levels after TRIM32 expression in the second penal). However, when TRIM32 is expressed and the UPS is inhibited a strong accumulation of poly-ubiquitinated Myc can be observed.

These experiments clearly show that TRIM32 ubiquitinates Myc and thereby labels it for degradation via the UPS.

EXAMPLE 4

Binding of TRIM32 to Argonaute 1 and Effect on MicroRNAs

When TRIM32 is expressed in cells, it is usually localized in distinct punctuated spots in the cytoplasm. This distribution resembles on the localization pattern of the protein Argonaute-1 (Ago1). Therefore, EGFP-tagged TRIM32 and Myc-tagged Ago1 are co-expressed in NIH3T3 cells. Interestingly, a perfect colocalization of TRIM32 positive spots with Ago1 positive spots is found. To further find out whether this colocalization indicates a real physical interaction, protein extracts are prepared from embryonic mouse brains (E14.5) and TRIM32 and Ago1 are precipitated from these brains with specific antibodies. As a control-IP a TRIM32 antibody is used that previously has been blocked with the corresponding TRIM32 peptide. After precipitation with the anti-TRIM32 antibody we are able to detect Ago1 and after Ago1 precipitation TRIM32 is detectable. These results indicate that TRIM32 and Ago1 interact with each other FIG. 4a). The Ago1 protein is part of the RISC and this complex is an essential component of the micro-RNA pathway. Therefore it is tested if expression TRIM32 regulates the levels of specific miRNA's. To this end, neural stem cells are transfected with expression plasmids for EGFP or EGFP-tagged TRIM32 as described above. After four days of cultivation the miRNA profiles of the transfected cells are measured with an miR-CURY LNA Array microRNA (Exiqon). Most of the detected miRNA's are unchanged in their expression level, but the miRNA's 146b, 489 and 615 are significantly down regulated (FIG. 4b), while the miRNA's 26a and 129-3-p show a significant upregulation (FIG. 4c). These results are verified via a quantitative PCR approach (data not shown).

These experiments show that TRIM32 interacts with the Argonaute-1 protein and thereby regulates the levels of specific micro-RNAs.

REFERENCES

Agrawal, S., and Zhao, Q., *Curr. Opin. Chem. Biol.* 2, 519-528 (1998).

Albor A, El-Hizawi S, Horn E J, Laederich M, Frosk P, Wrogemann K, Kulesz-Martin M. (2006), *J. Biol. Chem.*, 281, 25850-66.

Auer, M., Moore, K. J., Meyer-Almes, F.-J., Guenther, R., Pope, A. J., and Stoeckli, K. A., (1998) *Drug Discovery Today* 3, 457-465.

Berg, T., Cohen, S. B., Desharnais, J., Sonderegger, C., Maslyar, D. J., Goldberg, J., Boger, D. L. and Vogt, P. K. (2002), *Proc Natl Acad Sci USA,* 99, 3830-3835.

Bennett, C. F., Chiang, M. Y., Chan, H., Shoemaker, J. E., and Mirabelli, C. K., *Mol. Pharmacol.* 41, 1023-1033 (1992).

Betschinger J, Mechtler K, Knoblich J A. (2006), *Cell,* 124, 1241-53.

Birikh, K. R., Heaton, P.A., and Eckstein, F., *Eur. J. Biochem.* 245, 1-16 (1997).

Braasch, D. A., and Corey, D. R., *Biochemistry* 41, 4503-4510 (2002).

Brodeur, G. M., Seeger, R. C., Schwab, M., Varmus, H. E. and Bishop, J. M. (1984), *Science,* 224, 1121-1124.

Brummelkamp, T. R., Bernards, R., and Agami, R., *Science* 296, 550-553 (2002a).

Brummelkamp, T. R., Bernards, R., and Agami, R., *Cancer Cell* 2, 243-247 (2002b).

Buchschacher, G. L. Jr., and Wong-Staal, F., *Blood* 95, 2499-2504 (2000).

Calegari, F., Haubensak, W., Yang, D., Huttner, W. B. and Buchholz, F. (2002). *Proc. Natl. Acad. Sci. USA* 99, 14236-14240.

Calin G A, Dumitru C D, Shimizu M, Bichi R, Zupo S, Noch E, Aldler H, Rattan S, Keating M, Rai K, Rassenti L, Kipps T, Negrini M, Bullrich F, Croce C M. (2002), *Proc Natl Acad Sci USA,* 99, 15524-9.

Calin G A, Liu C G, Sevignani C, Ferracin M, Felli N, Dumitru C D, Shimizu M, Cimmino A, Zupo S, Dono M, Dell'Aquila M L, Alder H, Rassenti L, Kipps T J, Bullrich F, Negrini M, Croce C M. (2004), *Proc Natl Acad Sci USA.*, 101, 11755-60.

Chiang A P, Beck J S, Yen H J, Tayeh M K, Scheetz T E, Swiderski R E, Nishimura D Y, Braun T A, Kim K Y, Huang J, Elbedour K, Carmi R, Slusarski D C, Casavant T L, Stone E M, Sheffield V C. (2006), *Proc Natl Acad Sci USA.,* 103, 6287-92.

Conti L., et al. (2005). *PLoS Biol.* September; 3(9):e283. Epub 2005 Aug. 16.

Cooper M. A., *Drug Discovery Today*, Volume 11, Issues 23-24, December 2006, Pages 1061-1067.

Earnshaw, D. J., and Gait, M. J., *Antisense Nucleic Acid Drug Dev.* 7, 403-411 (1997).

Eigen, M., and Rigler, R. (1994) *Proc. Natl. Acad. Sci. USA* 91, 5740-5747.

Elbashir, S. M., et al., (2001) *Nature* 411, 494-498.

Felsher D W and Bishop J M (1999), *Mol. Cell,* 4, 199-207.

Follenzi, A., and Naldini, L., *Methods Enzymol.* 346, 454-465 (2002).

Galderisi, U., Cascino, A., and Giordano, A., *J. Cell Physiol.* 181, 251-257 (1999).

Garraway L A, Sellers W R. (2006), *Nat Rev Cancer,* 6, 593-602.

Gershkovich, A. A. and Kholodovych, V. V. (1996), *J Biochem Biophys Meth* 33, 135.

Gewirtz, A. M., *Curr. Opin. Hematol.* 5, 59-71 (1998).

Grandori C and Eisenman R N (1997). *Trends Biochem Sci.,* 22, 177-81.

Hampel, A., *Prog. Nucleic Acid Res. Mol. Biol.* 5, 1-39 (1998).

Hatfield P M, Canis J, and Vierstra R D (1990) *J Biol Chem* 265, 15813-7

Hatfield P M, and Vierstra R D (1992) *Biol Chem* 267, 14799-803

He, et al. *Cytometry* A. 2003 October; 55(2):71-85.

He L, Thomson J M, Hemann M T, Hemando-Monge E, Mu D, Goodson S, Powers S, Cordon-Cardo C, Lowe S W, Hannon G J, Hammond S M. (2005), *Nature,* 435, 828-33.

Höglinger G U, Rizk P, Muriel M P, Duyckaerts C, Oertel W H, Caille I, Hirsch E C. *Nat Neurosci.* 2004 July; 7(7):726-35.

Hosseinkhani et al., (2007), *J Biomed Mater Res A.*, August 9.

Irie, A., Anderegg, B., Kashani-Sabet, M., et al., *Antisense Nucleic Acid Drug Dev.* 9, 341-349 (1999).

Jain, M. et al. (2002), *Science,* 297, 102-4.

Kafri, T., van Praag, H., Ouyang, L., Gage, F. H., and Verma, I. M., *J. Virol.* 73, 576-584 (1999).

Kettling, U., Koltermann, A., Schwille, P., and Eigen, M. (1998) *PNAS. USA* 95, 1416-1420.

Koltermann, A., Kettling, U., Bieschke, J., Winkler, T., and Eigen, M. (1998) *PNAS. USA* 95, 1421-1426.

Kore, A. R., and Eckstein, F., *Biochemistry* 38, 10915-10918 (1999).

Kudryashova E, Kudryashov D, Kramerova I, Spencer M J. (2005), *J Mol Biol.*, 354, 413-24.

Lappalainen K. et al., *Antiviral Res.*, February; 23 (2): 119-130 (1994).

Lever, A. M., *Gene Ther.* 3, 470-471 (1996).

Li J. Y. et al., *NeuroRx.*, 2005 July; 2(3): 447-464.

Luther-Wyrsch, A., et al., *Hum. Gene Ther.* 12, 377-389 (2001).

Magde, D., Elson, E. L. & Webb, W. W. (1974) *Biopolymers* 13, 29-61.

Maiti, S., Haupts, U., and Webb, W. W. (1997) *Proc. Natl. Acad. Sci. USA* 94, 11753-11757.

Matayoshi, E. D., Wang G T, Krafft G A, Erickson J. (1990), *Science* February 23; 247 (4945): 954-8.

Morgan L., et al., *Neuroscience Letters*, Volume 395, Issue 2, 6 March 2006, Pages 143-148.

Murray, A. (1991), *Methods Cell Biol.* 36, 581-605.

Okita K, Ichisaka T, Yamanaka S. (2007), *Nature,* 448, 313-7.

Pelengaris, S., Khan, M. & Evan, G., (2002b), *Nat Rev Cancer,* 2, 764-7.

Rigler, R., and Widengren, J. (1990) *Bioscience* 3, 180-183.

Rigler, R., Mets, U., Widengren, J., and Kask, P. (1993) *Eur. Biophys. J.* 22, 169-175.

Rogers, M. V. (1997) *Drug Discovery Today* 2, 156-160.

Ross et al., 2000, *Nat Genet,* 24, 227-35.

Schwab, M., Alitalo, K., Klempnauer, K. H., Varmus, H. E., Bishop, J. M., Gilbert, F., Brodeur, G., Goldstein, M. and Trent, J. (1983), *Nature,* 305, 245-248.

Schwille, P., Meyer-Almes, F.-J., and Rigler, R. (1997) *Biophys. J.* 72, 1878-1886.

Selvin, (2000) *Nature Structural Biol.* 7(9), 730-734.

Shu T, Tseng H C, Sapir T, Stern P, Zhou Y, Sanada K, Fischer A, Coquelle F M, Reiner O, Tsai L H. (2006), *Neuron,* 49, 25-39.

Smith, S. M., Maldarelli, F., and Jeang, K. T., *J. Virol.* 71, 9713-9721 (1997).

Stark A, Brennecke J, Russell R B, Cohen S M. (2005), *Genes Dev.*, 19, 2261-4.

Sui, G., Soohoo, C., Affar, E. B., Gay, F., Shi, Y., Forrester, W. C., and Shi, Y., *PNAS USA* 99, 5515-5520 (2002).

Thews E, Gerken M, Eckert R, Zapfel J, Tietz C, Wrachtrup, *J. Biophys J.* (2005) September; 89(3):2069-76. Epub 2005 Jun. 10

Vaish, N. K., Kore, A. R., and Eckstein, F., *Nucleic Acids Res.* 26, 5237-5242 (1998).

van de Wetering, M., Sancho, E., Verweij, C., de Lau, W., Oving, I., Hurlstone, A., van der Horn, K., Batlle, E., Coudreuse, D., Haramis, A. P., Tjon-Pon-Fong, M., Moerer, P., van den Born, M., Soete, G., Pals, S., Eilers, M., Medema, R. and Clevers, H. (2002), *Cell*, 111, 241-250.

VandenDriessche, T., Naldini, L., Collen, D., and Chuah, M. K., *Methods Enzymol.* 346, 573-589 (2002).

Wernig M, Meissner A, Foreman R, Brambrink T, Ku M, Hochedlinger K, Bernstein B E, Jaenisch R. (2007), *Nature*, 448, 318-24.

Winner Beate, Martin Geyer, Sebastien Couillard-Despres, Robert Aigner, Ulrich Bogdahn, Ludwig Aigner, Georg Kuhn, and Jurgen Winkler, *Experimental Neurology*, Volume 197, Issue 1, January 2006, Pages 113-121.

Yokota T, Mishra M, Akatsu H, Tani Y, Miyauchi T, Yamamoto T, Kosaka K, Nagai Y, Sawada T, Heese K. (2006), *Eur J Clin Invest.*, 36, 820-30.

Yu, et al., (2002). *Proc Natl Acad Sci USA*, April 30; 99(9): 6047-52.

---

The invention claimed is:

1. A method for modulating differentiation and proliferation potential of stem cells or progenitor cells comprising modulating TRIM32 protein expression and/or activity levels in the cells.

2. The method of claim 1, wherein the cells are human cells and the TRIM NHLTRIM32 protein is a human TRIM32 protein encoded by a polynucleotide comprising the sequence of SEQ ID NO:1.

3. The method of claim 1, comprising decreasing the expression and/or activity of the TRIM32 protein, thereby promoting a proliferation potential and decreasing a differentiation potential of the cells.

4. The method of claim 3, further defined as an in vitro method comprising cultivating the cells in a medium that contains a nucleotide inhibitor that inhibits the expression and/or activity of the TRIM32 protein.

5. The method of claim 3, further defined as an in vitro method comprising transfecting the cells with an antisense molecule, a DNA molecule encoding a ribozyme, or an siRNA, wherein the inhibitory molecule is directed against the a TRIM32 protein comprising an amino acid sequence of SEQ ID NO:2.

6. The method of claim 5, wherein the inhibitory molecule comprises the sequence of SEQ ID NO:7.

7. The method of claim 1, wherein the cells are somatic human stem cells further defined as neural stem cells, hematopoietic stem cells, mesenchymal stem cells, skin stem cells, and/or umbilical cord blood stem cells.

8. The method of claim 1, wherein the somatic stem cells or progenitor cells are in a subject, the method further comprising:
    obtaining a therapeutically effective amount of one or more nucleotide inhibitors that inhibit the level of expression and/or activity of a TRIM32 protein in the cells; and
    administering the one or more nucleotide inhibitors to the subject.

9. The method of claim 8, wherein the nucleotide inhibitor is an antisense molecule, a DNA molecule encoding a ribozyme, or an siRNA.

10. The method of claim 9, wherein the inhibitory molecule comprises the sequence of SEQ ID NO:7.

11. The method of claim 8, wherein the subject is a human.

12. A culture medium comprising nutrients and supplements required for cultivation of cells and a nucleotide inhibitor that inhibits the expression and/or activity of a TRIM32 protein.

13. A method for determining whether a test compound has the ability to modulate proliferation and/or differentiation potential of stem cells or progenitor cells comprising:
    obtaining a test compound; and
    testing whether the test compound is able to modulate an ability of a TRIM32 protein to transfer ubiquitin from a ubiquitin conjugating enzyme E2 to Myc or binding of TRIM32 protein to Argonaute-1, wherein a change in a level or activity of the TRIM32 protein in the presence of the test compound as compared to a level of TRIM32 activity in the absence of the test compound is indicative of the compound's ability to modulate the proliferation and/or differentiation potential of stem cells or progenitor cells.

14. The method of claim 13, wherein:
    the TRIM32 protein is encoded by a polynucleotide having the sequence of SEQ ID NO:1.

15. The method of claim 14, wherein a test compound is tested for its ability to promote the proliferation potential of stem cells or progenitor cells by determining whether the compound has an inhibitory effect on the TRIM32 protein.

16. The method of claim 15, further defined as a method for identifying nucleotide inhibitors that have the ability to promote the proliferation potential of stem cells or progenitor cells.

17. A method of generating a TRIM32 protein inhibitor that has an ability to promote proliferation potential of stem cells and/or progenitor cells comprising:
    obtaining:
        a DNA molecule of SEQ ID NO: 1, or a variant encoding a polypeptide with at least about 80% identity with a TRIM32 protein of SEQ ID NO:2, or a fragment thereof or a complement thereto; or
        a TRIM32 protein of SEQ ID NO:2, or a variant with at least about 80% identity or a fragment thereof; and
    using the DNA molecule or TRIM32 protein to generate a modulator of biological function of a TRIM32 protein, wherein the biological function is an ability of the TRIM32 protein to transfer ubiquitin from a ubiquitin conjugating enzyme E2 to Myc or binding of TRIM32 protein to Argonaute-1.

18. A pharmaceutical composition, comprising an amount of one or more nucleotide inhibitors effective to inhibit expression and/or activity of a TRIM32 protein in somatic stem cells or progenitor cells in a subject, and a pharmaceutically acceptable carrier.

19. The pharmaceutical composition of claim 18, wherein the nucleotide inhibitor is an antisense molecule, a DNA molecule encoding a ribozyme, or an siRNA.

20. The pharmaceutical composition of claim 19, wherein the inhibitory molecule comprises the sequence of in SEQ ID NO:7.

* * * * *

UNITED STATES PATENT AND TRADEMARK OFFICE
CERTIFICATE OF CORRECTION

PATENT NO. : 8,431,398 B2
APPLICATION NO. : 12/680493
DATED : April 30, 2013
INVENTOR(S) : Juergen Knoblich et al.

It is certified that error appears in the above-identified patent and that said Letters Patent is hereby corrected as shown below:

In the Claims:

In claim 2, column 47, line 7, delete "TRIM NHL".

In claim 5, column 47, line 22, delete "the".

Signed and Sealed this
Eleventh Day of June, 2013

Teresa Stanek Rea
*Acting Director of the United States Patent and Trademark Office*